United States Patent
Firoozmand et al.

(10) Patent No.: US 11,447,739 B2
(45) Date of Patent: Sep. 20, 2022

(54) YEAST AND BACTERIA AS STABILIZERS IN EMULSIONS OF OIL AND WATER

(71) Applicant: Hassan Firoozmand, Vancouver (CA)

(72) Inventors: Hassan Firoozmand, Vancouver (CA); Dérick Rousseau, Toronto (CA)

(73) Assignee: Hassan Firoozmand, Vancouver (CA)

( * ) Notice: Subject to any disclaimer, the term of this patent is extended or adjusted under 35 U.S.C. 154(b) by 74 days.

(21) Appl. No.: 15/128,113

(22) PCT Filed: Mar. 25, 2014

(86) PCT No.: PCT/CA2014/050307
§ 371 (c)(1),
(2) Date: Sep. 22, 2016

(87) PCT Pub. No.: WO2015/143532
PCT Pub. Date: Oct. 1, 2015

(65) Prior Publication Data
US 2017/0121671 A1    May 4, 2017

(51) Int. Cl.
*C12N 1/20* (2006.01)
*C12N 1/18* (2006.01)
*A23D 7/005* (2006.01)
*A23L 29/00* (2016.01)
*A23L 29/10* (2016.01)
*C09K 23/00* (2022.01)

(52) U.S. Cl.
CPC ............. *C12N 1/20* (2013.01); *A23D 7/0053* (2013.01); *A23L 29/065* (2016.08); *A23L 29/10* (2016.08); *C09K 23/00* (2022.01); *C12N 1/18* (2013.01); *A23V 2002/00* (2013.01)

(58) Field of Classification Search
None
See application file for complete search history.

(56) References Cited

U.S. PATENT DOCUMENTS 3,995,066 A * 11/1976 Muys .................. A23D 7/0056
426/62

FOREIGN PATENT DOCUMENTS

DE          242561        *  2/1987

OTHER PUBLICATIONS

Shima et al., J. Biosci. Bioeng. 103(3): 278-281 (2007).*
O'Riordan et al., Glycobiology 24(3): 220-236 (2014; published online Jan. 6, 2014).*
Moskowitz, "Cheesy Sauce", Vegan Brunch, p. 217, Da Capo Press, Philadelphia, PA (2009).*
Voisin, https://blog.fatfreevegan.com/2011/10/what-the-heck-is-nutritional-yeast.html, published Oct. 26, 2011, accessed Jan. 31, 2019.*
Wampler, "Rosemary Olive Oil Bread", https://www.tablefortwoblog.com/rosemary-olive-oil-bread, published Jan. 4, 2013, accessed Jul. 24, 2019.*
The Frugal Girl, https://www.thefrugalgirl.com/wednesday-baking-troubleshooting-yeast-bread/, published Feb. 24, 2010, accessed Jul. 25, 2019.*

(Continued)

*Primary Examiner* — Erin M. Bowers
(74) *Attorney, Agent, or Firm* — Eric L. Lane; Green Patent Law

(57) ABSTRACT

A stable emulsion, comprising oil, water and a stabilizer, wherein said stabilizer is selected from a single-cell microorganism.

17 Claims, 33 Drawing Sheets

(56) References Cited

OTHER PUBLICATIONS

Wikipedia, https://web.archive.org/web/20120720152521/https://en.wikipedia.org/wiki/Beeswax, archived Jul. 20, 2012, accessed Jan. 9, 2020.*
Vogue Australia, https://www.vogue.com.au/beauty/makeup/green-your-beauty-bag-the-case-for-raw-and-vegan-skincare-products/image-gallery/97bd9bfdb1e7bfc8334548f36570df3f, Feb. 3, 2014.*
Younkin, https://barefeetinthekitchen.com/whole-wheat-tortillas/, published Jul. 15, 2011, accessed Apr. 7, 2021.*
Lallemand, https://www.lallemand.com/BakerYeastNA/eng/PDFs/FERMAID.PDF, published Feb. 2000, accessed Apr. 6, 2021.*
Whole New Mom, https://wholenewmom.com/five-ingredient-salad-dressing-recipe-our-new-favorite/, published Feb. 28, 2013, accessed Jan. 11, 2022.*
Flickinger et al., Lipids 38: 129-132 (2003).*
International Preliminary Report on Patentability dated Sep. 27, 2016 in related International Patent Application No. PCT/CA2014/050307.
Office Action dated Jul. 28, 2017 in related Canadian Patent Application No. 2,943,568.
Dorobantu, L.S., et al., "Stabilization of oil-water emulsions by hydrophobic bacteria", Appl. Env. Microbiol., vol. 70, No. 10, pp. 6333-6336, Oct. 2004, ISSN: 0099-2240.
Hou, R.C.W., et al., "Increase of viability of entrapped cells of *Lactobacillus delbrueckii* ssp. *bulgaricus* in artifical sesame oil emulsions", J. Dairy Sci. vol. 86, 2003.
Srivastava, S.P., et al., "Physiochemical studies on the water-yeast cells-gas-oil system", J. Appl. Chem., vol. 20, pp. 105-108, Apr. 1970, ISSN: 2356-7171.
Lead-Calderon, F., et al., "Solid-stabilized emulsions", Curr. Opin. Colloid Interface Sci., vol. 13, pp. 217-227, 2008, ISSN: 1359-0294.
Binks, B.P., "Particles as surfactants—similarities and differences", Curr. Opin. Colloid Interface Sci., vol. 7, pp. 21-41, 2002, ISSN: 1359-0294.
Binks, B.P., et al., "Solid wettability from surface energy components: relevance to Pickering emulsions", Langmuir, vol. 18, pp. 1270-1273, 2002, ISSN: 0743-7463.
International Search Report dated Dec. 1, 2014 in related International Patent Application No. PCT/CA2014/050307.
Office Action dated Aug. 13, 2018 in related Canadian Patent Application No. 2,943,568.
Furtado, et al., Breaking oil-in-water emulsions stabilized by yeast, Colloids and Surfaces B: Biointerfaces 128 (2015) 568-576.

* cited by examiner

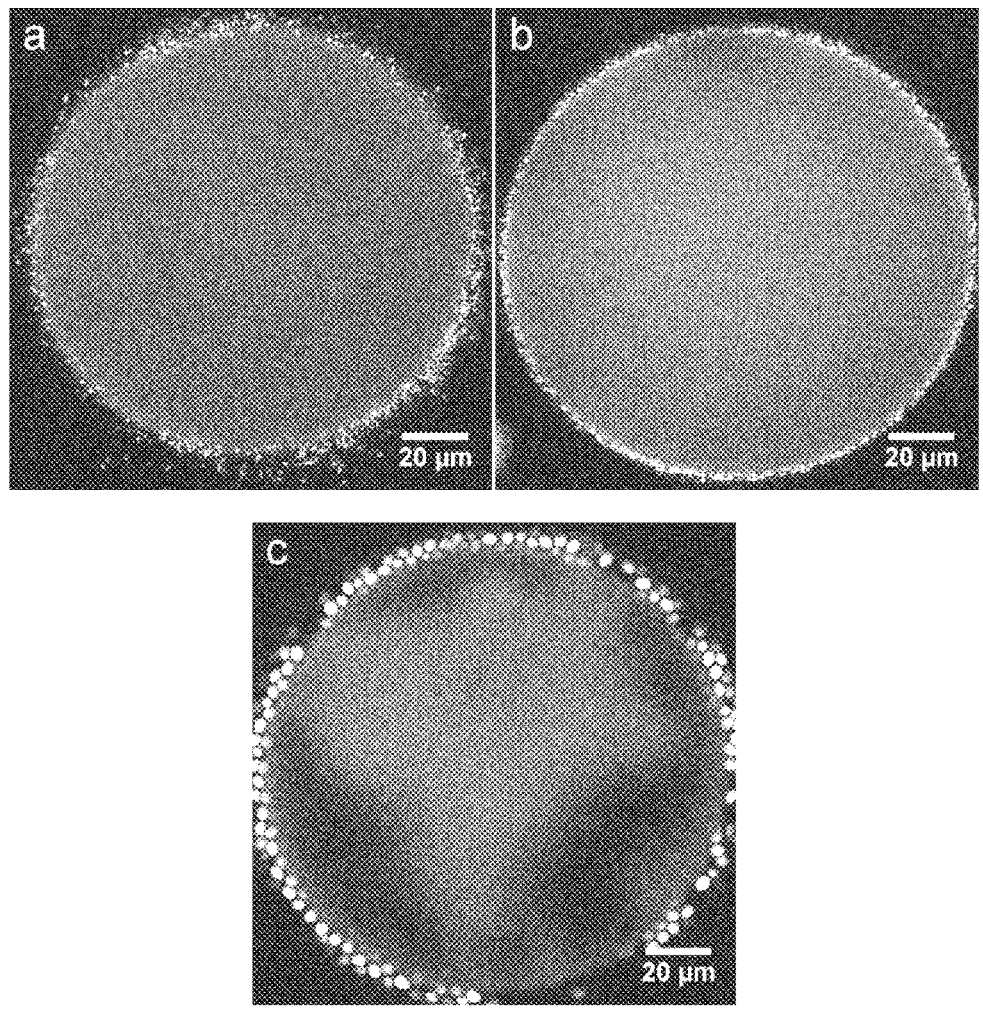
Figure 33 (a, b, c)

YEAST AND BACTERIA AS STABILIZERS IN EMULSIONS OF OIL AND WATER

FIELD OF THE INVENTION

The present invention relates to compositions, preferably liquid compositions comprising stable oil-in-water emulsions without the addition of one or more surfactants and/or emulsifiers in the liquid or solid state. The present invention also relates to the emulsions used in the compositions, wherein the emulsions are formed by the combination of oil plus water as well as a single cell microorganism, in one embodiment yeast, preferably Baker's yeast, or bacteria, preferably probiotic bacteria, most preferably inactivated bacteria, such as the genus *Lactobacillus, Lactococcus* or *Streptococcus*, or combinations thereof added when forming the emulsion. A stable emulsion generally refers to the ability of the emulsion to resist change in its properties over time. The single cell microorganism in the emulsion is capable of residing at the oil-water interface. Oil-in-water emulsions stabilized with these cells form stable emulsions, even in the absence of an emulsifier between the two phases.

BACKGROUND OF THE INVENTION

Emulsions are widely used in the chemical, food, pharmaceutical, cosmetic and agrochemical industries. Emulsions usually consist of two or more mutually-insoluble phases, such as oil and water, which try to lower their free energy by bulk phase-separating the oil and water. An emulsion may be stabilized against phase separation by addition of biopolymers such as hydrocolloids and proteins, small-molecule surfactants such as lecithin and polysorbates and solid micron- and nano-sized particles. When an emulsion is stabilized by solid particles, it is called a Pickering emulsion (Pickering, 1907). Pickering emulsions stabilized by insoluble solid particles show superior stability against coalescence compared with those stabilized with hydrocolloids, proteins and surfactants (Dickinson, 2009). The stabilization mechanism of Pickering emulsions is due to the formation of a steric barrier by solid particles around the dispersed droplets (Dickinson, 2010). Once absorbed at the liquid-liquid interface, the desorption energy of the particles from the interface is high, and the particles remain at the interface. In spite of the high potential of the use of colloidal particles as Pickering stabilizers, there are only a limited number of colloidal particles that may be used in the food industry (de Folter, van Ruijven, & Velikov, 2012; Dickinson, 2010; Liu & Tang, 2013; Yusoff & Murray, 2011). Examples of organic particles for use in food applications include: fat particles (Poortinga, 2008), β-lactoglobulin (Nguyen, Nicolai, & Benyahia, 2013), zein protein (de Folter, et al., 2012), hydrophobic cellulose particles (Wege, Kim, Paunov, Zhong, & Velev, 2008), soy protein nanoparticles (Liu, et al., 2013) and quinoa starch particles (Rayner, Timgren, Sjoo, & Dejmek, 2012). However, these groups of particles suffer from key limitations. Some of these, such as fat particles, are temperature-sensitive and will melt at typical processing temperatures. Others, like starch granules, lose their functionally. β-lactoglobulin, zein protein and soy protein nanoparticles can only be made on a lab-scale whereas hydrophobic cellulose particles have a relatively broad particle size distribution, which makes them less efficient as Pickering stabilizers. Preferably, the particles should be spherical-shaped with a defined particle size range. There are some limitations with the production of colloidal particles. Either the production processes of colloidal particles are very energy-intensive and expensive or they are complex and difficult for implementation in industry (Velikov & Pelan, 2008). It is rather difficult to produce food-grade particles with a defined size range, and most materials being used to produce colloidal particles are not acceptable in food systems (Liu & Tang, 2013). Overall, robust readily-available food-grade particles are scarce and/or production techniques for food-grade-particles are restricted by legislative regulations and/or are limited to small/lab-scale applications.

It has been reported while using a mixture of petroleum hydrocarbons, water and mineral salts as a medium to grow yeast for feed production, the produced yeasts formed a very stable emulsion by the Pickering stabilization mechanism in the growth culture (Srivasta, Singh, Baruah, Krishna, & Iyengar, 1970). This ability of other single-celled microorganisms nesting at the petroleum hydrocarbon-water interface has been reported in the scientific literature (Rosenberg & Rosenberg, 1985). A decade ago, it was shown how to make Pickering emulsions using n-alkane-degrading bacteria to stabilize n-hexadecane-water mixtures (Dorobantu, Yeung, Foght, & Gray, 2004). More recently, Pickering emulsions were made with *Staphylococcus aureus, Bacillus subtilis, Bacillus cereus*, and *Escherichia coli* DH5α, as colloidal particles with the addition of chitosan (biopolymer) to hold these cells at the oil-water interface.

When the dispersed phase in an emulsion has a higher volume fraction than that of the continuous phase, the emulsion is called a high internal phase ratio emulsion (Lissant 1966; Williams 1991; Reynolds, Gilbert et al. 2000). These emulsions are known by variety of names including highly-concentrated emulsions, (Princen, Aronson et al. 1980; Babak and Stebe 2002) and gel emulsions (Kunieda, Solans et al. 1987). High internal phase ratio emulsions have practical applications in foods, cosmetics (Jager-Lezer, Tranchant et al. 1998), topical drug delivery systems (Riess and Weers 1996), extraction of antibiotics and pollutants (Lye and Stuckey 1998) and other important industrial applications (Krafft and Riess 1994; Babak and Stebe 2002). Despite the superiority of the particles to stabilize an oil in water emulsion in comparison to surfactants and biopolymers, the use of particles to make a oil in water Pickering emulsion with an internal phase ratio higher than 0.71 did not work (Binks and Lumsdon 2000; Kralchevsky, Ivanov et al. 2005; Masalova and Kharatyan 2013).

Accordingly, there is a need for the production of food-grade stable emulsions comprising edible single cell microorganisms.

There is also need for oil-in-water emulsions that are stable and have a high oil:water weight ratio.

SUMMARY OF THE INVENTION

According to one aspect, there is provided a stable emulsion, in one embodiment a stable oil-in-water emulsion, comprising oil, water and a stabilizer, wherein said stabilizer is selected from a at least one particle, preferably selected from at least one single-cell microorganism, preferably biologically inactive, more preferably an edible biologically inactive single-cell microorganism. In one embodiment said single-cell microorganism is selected from yeast, preferably Baker's yeast, the genus *Lactobacillus, Lactococcus, Streptococcus* and combinations thereof, preferably *Lactobacillus acidophilus, Lactobacillus casei, Lactobacillus crispatus, Lactobacillus gasseri, Lactobacillus johnsonii, Lactobacillus rhamnosus, Lactobacillus reuteri, Lactobacillus paracasei, Lactobacillus plantaru, Lactobacillus fermentum, Lactococcus lactis, Lactococcus cremoris, Streptococcus thermophilus and combinations thereof. Preferably said biologically inactive single-cell microorganism resides at or in an oil-water interface of said emulsion. In one embodiment, said stabilizer comprises a combination of an inactive and an active single-cell microorganism.

According to yet another embodiment, the stable oil-in-water emulsion comprises from about 0.01 wt % to about 99 wt % oil, preferably from about 1 wt % to about 80 wt % oil, even more preferably from about 50 wt % oil, most preferably from about 50 wt % to about 80 wt % oil, and from about 0.001 wt % to about 10 wt % of at least one single-celled microorganism, preferably from about 1 wt % to about 8 wt %, most preferably from about 2 wt % to about 7 wt %.

According to yet another embodiment, said stable oil-in-water emulsion further comprises a biopolymer, protein, polysaccharide or a combination thereof, preferably in an amount of from about 0.0001 wt % to about 10 wt %, more preferably from about 0.001 wt % to about 5 wt %, and most preferably from about 0.01 wt % to about 4 wt %. According to yet another embodiment, said oil-in-water emulsion further comprises at least one surfactant, surface-active material or a combination thereof, in an amount of from about 0.0001 wt % to about 10 wt %, preferably from about 0.001 wt % to about 5 wt %, and most preferably from about 0.01 wt % to about 4 wt % of the emulsion.

According to yet another embodiment, said stable oil-in-water emulsion further comprises at least one flavouring agent.

In yet another embodiment, said stable oil-in-water emulsion further comprises at least one colouring agent.

In yet another embodiment, said stable oil-in-water emulsion further comprises at least one acidulant.

In yet another embodiment, said stable oil-in-water emulsion further comprises at least one salt.

In yet another embodiment, said stable oil-in-water emulsion further comprises at least one antioxidant.

In yet another embodiment, said stable oil-in-water emulsion further comprises at least one preservative, preferably selected from the group consisting of ascorbic acid, benzoic acid, sorbic acid, acetic acid and combinations thereof in the acid or salt form.

In yet another embodiment, said stable oil-in-water emulsion further comprises at least one biopolymer.

In yet another embodiment, said stable oil-in-water emulsion further comprises at least one surfactant.

In yet another embodiment, said stable oil-in-water emulsion further comprises at least one vitamin.

In yet another embodiment, said stable oil-in-water emulsion further comprises at least one mineral.

Other ingredients known in the food industry, pharmaceutical industry, cosmetics industry, agrochemical industry or chemical industry known to a person of ordinary skill in the art may be added to the stable oil-in-water emulsion without compromising the present invention.

In yet another embodiment, said single-cell microorganism, preferably selected from a single-cell microorganism, preferably a plurality thereof, preferably said single-cell microorganism being active, inactive and combinations thereof alters at least one rheological property (including but not limited to viscosity, viscoelasticity, creep compliance and recovery) of said stable oil-in-water emulsion.

According to yet another aspect, there is provided the use of a single-celled microorganism, preferably active, inactive and combinations thereof, in one embodiment as a food-grade particle and in another embodiment as an industrial-grade particle.

Other uses include, but are not limited to, a texture modifier, a rheology modifier, as interfacial particles for encapsulation of molecules, preferably small molecules, for use in, including but not limited to, pharmaceuticals, nutraceuticals, agrochemicals, health supplements, personal health care products, sunscreen agents, fragrant agents and cosmetics.

According to yet another aspect, there is provided a process for stabilizing oil-in-water emulsions, preferably against oil droplet coalescence. Said process comprising adding at least one stabilizer selected from at least one single-cell microorganism, preferably active, inactive and combinations thereof, when forming an oil-in-water emulsion. Preferably said process further comprises the addition, preferably controlled addition of oil to an aqueous phase, said aqueous phase comprising at least one stabilizer and water, wherein said addition of said oil disperses oil into said aqueous phase resulting in a stable oil-in-water emulsion.

According to another aspect, there is provided compositions and methods for forming an oil-in-water emulsion, comprising oil and a liquid medium, preferably water; and at least one stability control agent selected from the group consisting of Baker's yeast, the genus *Lactobacillus*, *Lactococcus*, *Streptococcus* and combinations thereof, preferably *Lactobacillus casei*, *Lactobacillus crispatus*, *Lactobacillus gasseri*, *Lactobacillus johnsonii*, *Lactobacillus rhamnosus*, *Lactobacillus reuteri*, *Lactobacillus paracasei*, *Lactobacillus plantaru*, *Lactobacillus fermentum*, *Lactobacillus acidophilus*, *Lactococcus lactis*, *Lactococcus cremoris*, *Streptococcus thermophiles* and combinations thereof. The compositions may be used as a base to develop and improve a variety of oil-in-water emulsions suitable for, but not limited to the, food, pharmaceutical, cosmetics, chemical and agrochemical industries.

According to another aspect there is provided soft solid materials and methods to form same.

According to yet another aspect, there is provided an oil-in-water emulsion comprising Baker's yeast cells, *Lactobacillus* preferably *Lactobacillus casei*, *Lactobacillus crispatus*, *Lactobacillus gasseri*, *Lactobacillus johnsonii*, *Lactobacillus rhamnosus*, *Lactobacillus reuteri*, *Lactobacillus paracasei*, *Lactobacillus plantaru*, *Lactobacillus fermentum*, *Lactobacillus acidophilus*, *Lactococcus* preferably *Lactococcus lactis*, *Lactococcus cremoris*, *Streptococcus* preferably *thermophilus* and combinations thereof.

The invention further pertains to methods for the inactivation of Baker's yeast, *Lactobacillus* preferably *Lactobacillus casei*, *Lactobacillus crispatus*, *Lactobacillus gasseri*, *Lactobacillus johnsonii*, *Lactobacillus rhamnosus*, *Lactobacillus reuteri*, *Lactobacillus paracasei*, *Lactobacillus plantaru*, *Lactobacillus fermentum*, *Lactobacillus acidophilus*, *Lactococcus* preferably *Lactococcus lactis*, *Lactococcus cremoris*, and *Streptococcus* preferably *thermophilus*. According to yet another aspect, there is provided a method for making an oil-in-water emulsion comprising a Baker's yeast suspension, *Lactobacillus* preferably *Lactobacillus casei*, *Lactobacillus crispatus*, *Lactobacillus gasseri*, *Lactobacillus johnsonii*, *Lactobacillus rhamnosus*, *Lactobacillus reuteri*, *Lactobacillus paracasei*, *Lactobacillus plantaru*, *Lactobacillus fermentum*, *Lactobacillus acidophilus*, *Lactococcus* preferably *Lactococcus lactis*, *Lactococcus cremoris*, *Streptococcus* preferably *thermophilus* and combinations thereof.

In any of the above, the oil may be selected from vegetable oil, mineral oil, other oils of natural or synthetic origin and combinations thereof.

The term "stable" as used herein defines the ability of an oil-in-water emulsion to resist change in its properties over time, preferably for a period of time ranging from minutes to hours to years, depending on the intended use and the composition of the emulsion.

As used herein, the term "stabilized oil-in-water emulsion" refers to an oil-in-water emulsion that comprises at least one stabilizer (preferably at least one particle) that is at least one cell of biological origin, wherein said cell may be whole or in part, active or inactive, and combinations thereof.

BRIEF DESCRIPTION OF THE FIGURES

FIG. 8-a shows an emulsion made of 7 wt % yeast+70 wt % oil+23 wt % water. FIG. 8-b shows an emulsion made of 8 wt % yeast+65 wt % oil+27 wt % water and FIG. 8-c shows an emulsion made of 9 wt % yeast+60 wt % oil+31 wt % water.

Figure 8:
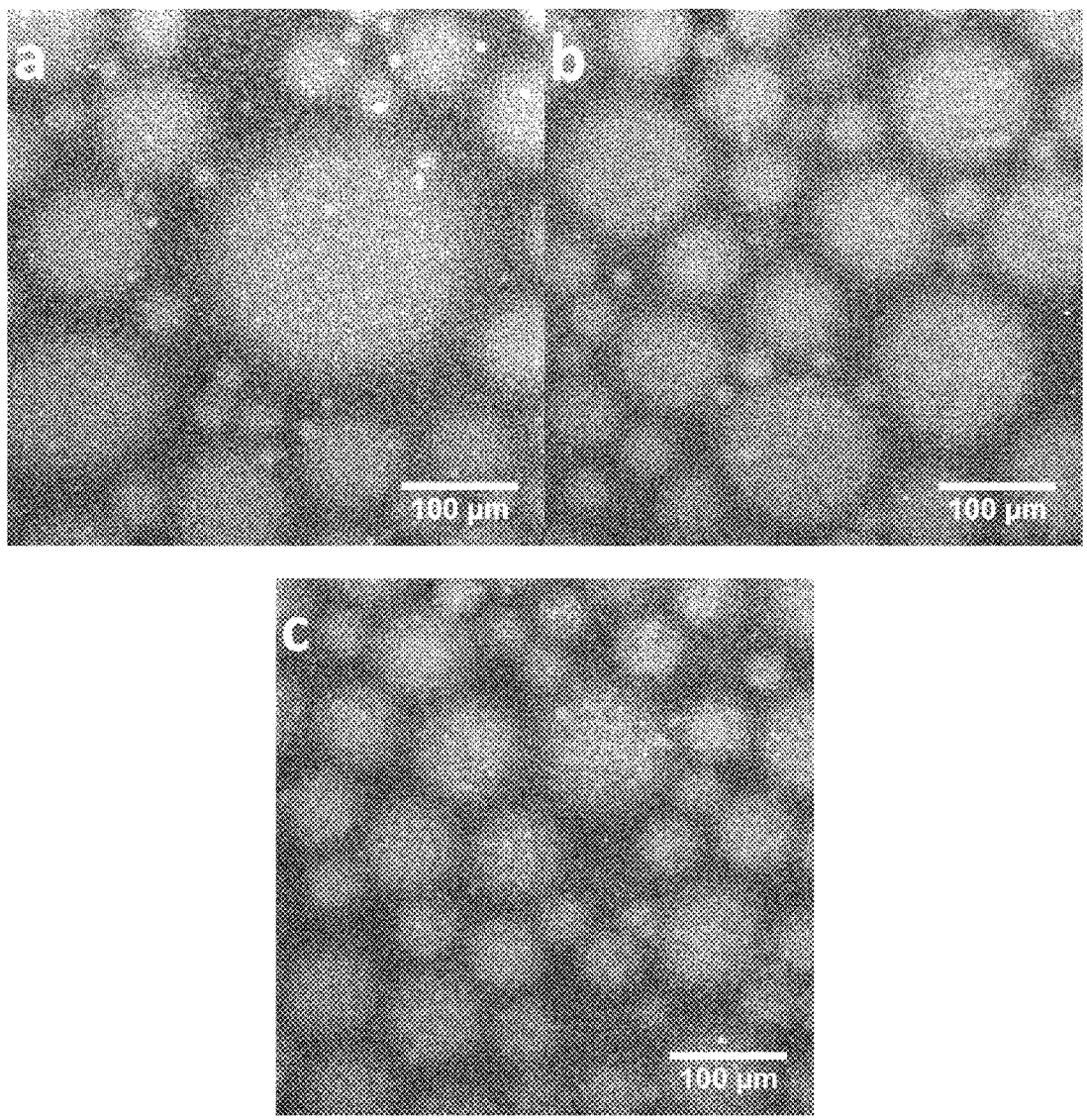
FIG. 8 (a, b, c) shows confocal laser scanning microscopy (CLSM) images of oil-in-water emulsions stabilized with Baker's yeast cells.

FIG. 21-a shows an emulsion made of 2 wt % *Streptococcus thermophilus*+80 wt % oil+18 wt % water, FIG. 8-b shows an emulsion made of 3 wt % *Streptococcus thermophilus*+80 wt % oil+17 wt % water and FIG. 8-*c* shows an emulsion made of 4 wt % *Streptococcus thermophilus*+80 wt % oil+16 wt % water.

Figure 22:
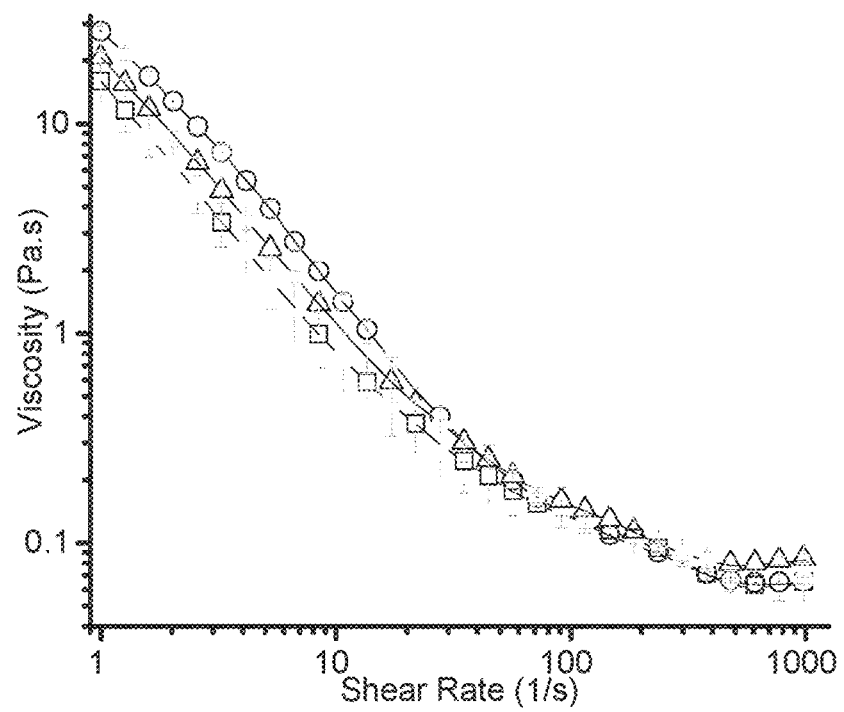

FIG. 22 depicts the shear viscosity versus shear rate profile of emulsion samples containing active (live) *Streptococcus thermophilus* bacterial cells at different concentrations: (□: 2 wt % *Streptococcus thermophilus*+80 wt % oil+18 wt % water); (○): 3 wt % *Streptococcus thermophilus*+80 wt % oil+17 wt % water); (Δ: 4 wt % *Streptococcus thermophilus*+80 wt % oil+16 wt % water).

Figure 23:
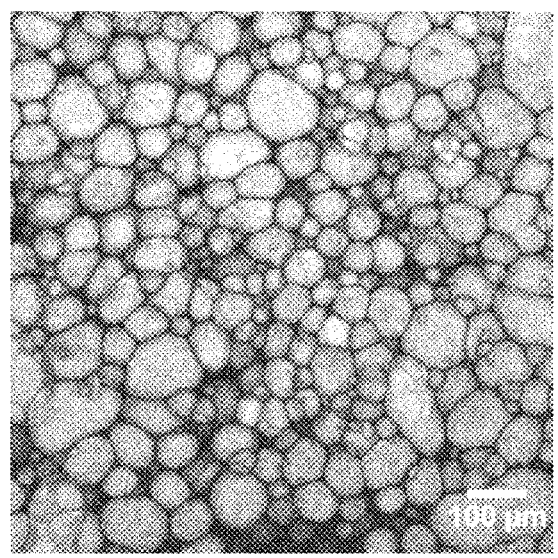

FIG. 23 shows the confocal laser scanning microscopy (CLSM) images of oil-in-water emulsions stabilized with *Streptococcus thermophilus* cells. The emulsion consists of 2 wt % *Streptococcus thermophilus*+80 wt % oil+18 wt % water.

Figure 24:
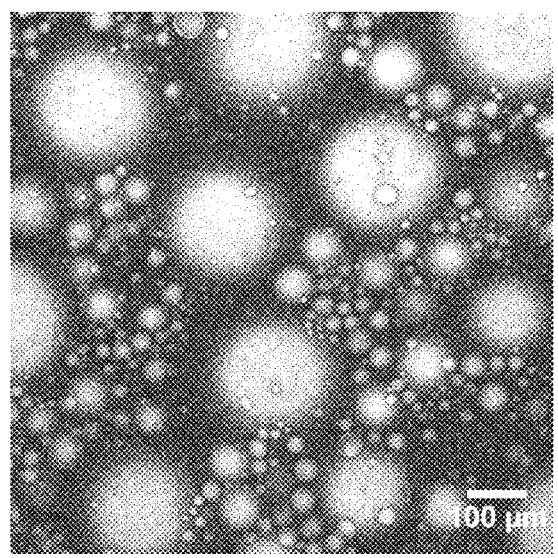

FIG. 24 shows the confocal laser scanning microscopy (CLSM) images of oil-in-water emulsions stabilized with *Streptococcus thermophilus* cells. The emulsion consists of 3 wt % *Streptococcus thermophilus*+70 wt % oil+27 wt % water.

Figure 25:
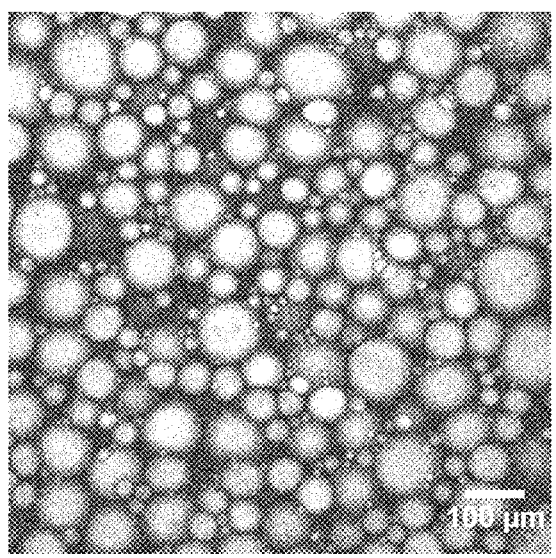

FIG. 25 shows the confocal laser scanning microscopy (CLSM) images of oil-in-water emulsions stabilized with *Streptococcus thermophilus* cells. The emulsion consists of 4 wt % *Streptococcus thermophilus*+70 wt % oil+26 wt % water.

Figure 26:
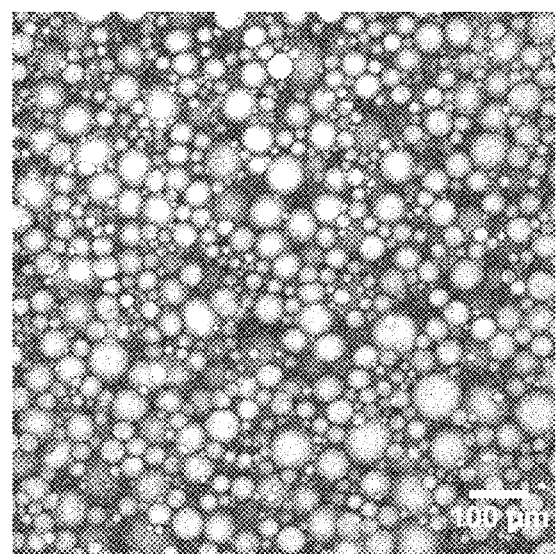

FIG. 26 shows the confocal laser scanning microscopy (CLSM) images of oil-in-water emulsions stabilized with *Streptococcus thermophilus* cells. The emulsion consists of 7 wt % *Streptococcus thermophilus*+60 wt % oil+33 wt % water.

Figure 27:
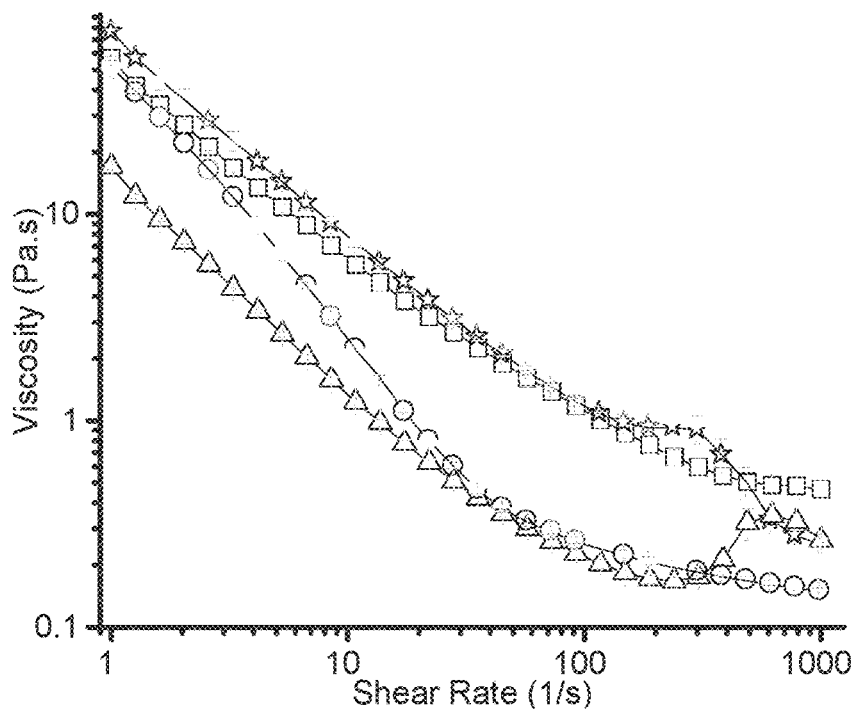

FIG. 27 shows the shear viscosity versus shear rate profile of emulsion samples of different compositions containing *Streptococcus thermophilus*: (○: 2 wt % *Streptococcus thermophilus*+80 wt % oil+18 wt % water); (Δ: 3 wt % *Streptococcus thermophilus*+70 wt % oil+27 wt % water); (☆: 4 wt % *Streptococcus thermophilus*+70 wt % oil+26 wt % water); (□: 7 wt % *Streptococcus thermophilus*+60 wt % oil+33 wt % water).

Figure 28:
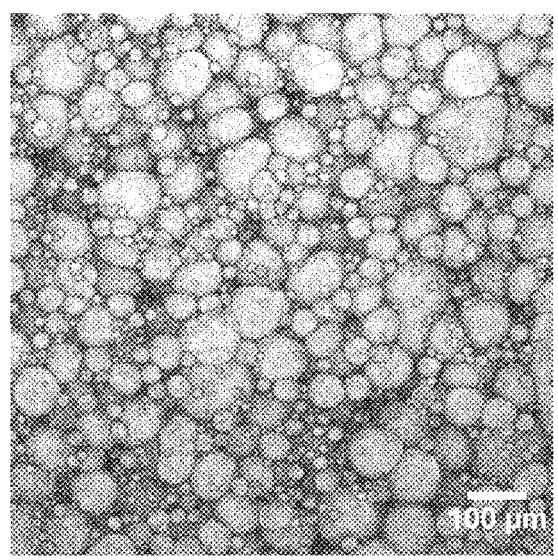

FIG. 28 shows the confocal laser scanning microscopy (CLSM) images of oil-in-water emulsions stabilized with *Lactobacillus acidophilus* cells. The emulsion consists of 2 wt % *Lactobacillus acidophilus*+75 wt % oil+23 wt % water.

Figure 29:
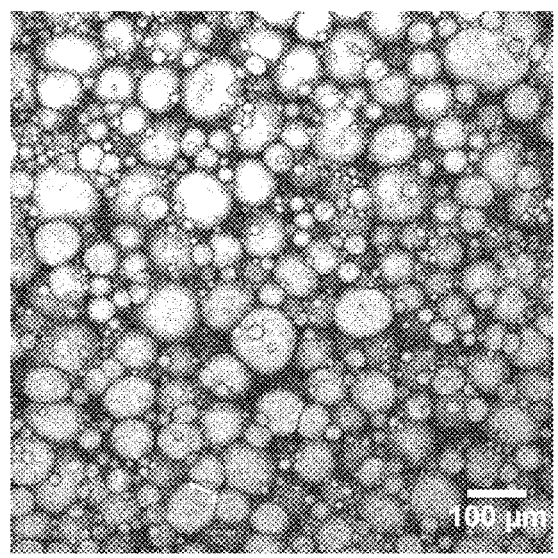

FIG. 29 shows the confocal laser scanning microscopy (CLSM) images of oil-in-water emulsions stabilized with *Lactobacillus acidophilus* cells. The emulsion consists of 3 wt % *Lactobacillus acidophilus*+70 wt % oil+27 wt % water.

Figure 30:
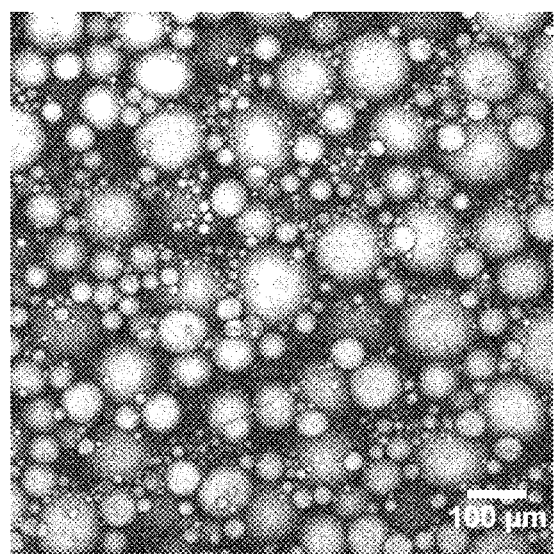

FIG. 30 shows the confocal laser scanning microscopy (CLSM) images of oil-in-water emulsions stabilized with *Lactobacillus acidophilus* cells. The emulsion consists of 4 wt % *Lactobacillus acidophilus*+65 wt % oil+31 wt % water.

Figure 31:
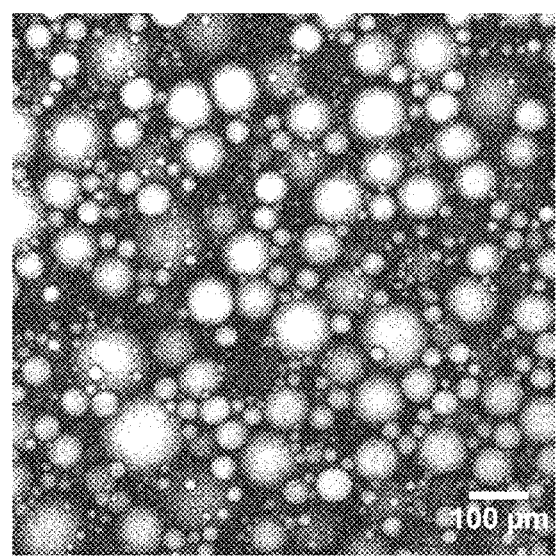

FIG. 31 shows the confocal laser scanning microscopy (CLSM) images of oil-in-water emulsions stabilized with *Lactobacillus acidophilus* cells. The emulsion consists of 5 wt % *Lactobacillus acidophilus*+60 wt % oil+35 wt % water.

Figure 32:
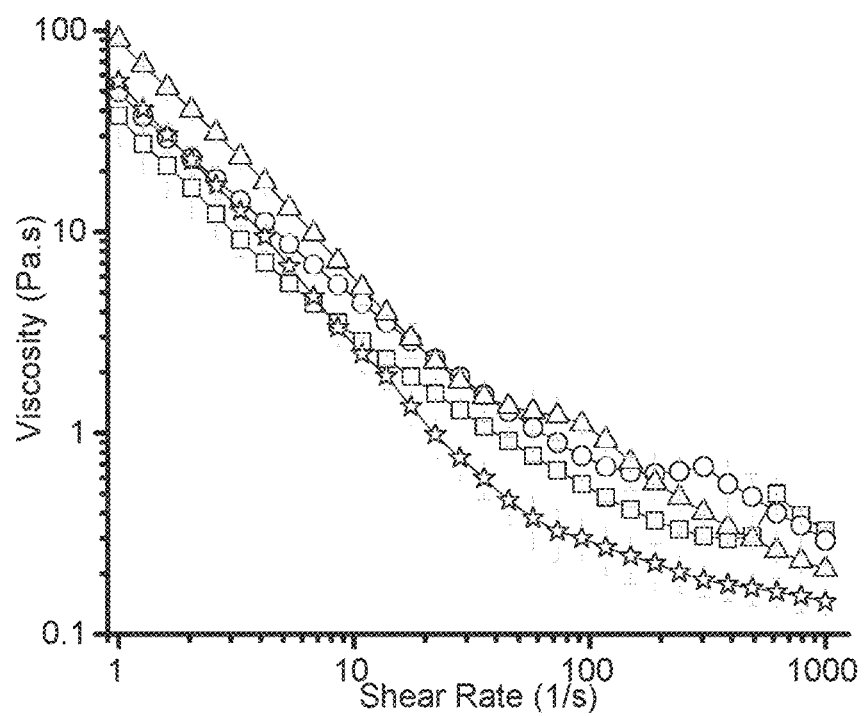

FIG. 32 shows the shear viscosity versus shear rate profile of emulsion samples of different compositions containing *Lactobacillus acidophilus*: (☆: 2 wt % *Lactobacillus acidophilus*+75 wt % oil+23 wt % water); (Δ: 3 wt % *Lactobacillus acidophilus*+70 wt % oil+27 wt % water); (○: 4 wt % *Lactobacillus acidophilus*+65 wt % oil+31 wt % water); (□: 5 wt % *Lactobacillus acidophilus*+60 wt % oil+35 wt % water).

FIG. 33 (*a, b, c*) show the confocal laser scanning microscopy (CLSM) images of oil droplets in oil-in-water emulsions stabilized with cells. FIG. 33-*a* shows one oil droplet stabilized with *Streptococcus thermophilus* cells, FIG. 33-*b* shows one oil droplet stabilized with *Lactobacillus acidophilus* cells and FIG. 33-*c* shows one oil droplet stabilized with Baker's yeast cells.

DETAILED DESCRIPTION OF THE PREFERRED EMBODIMENTS

Figure 1:
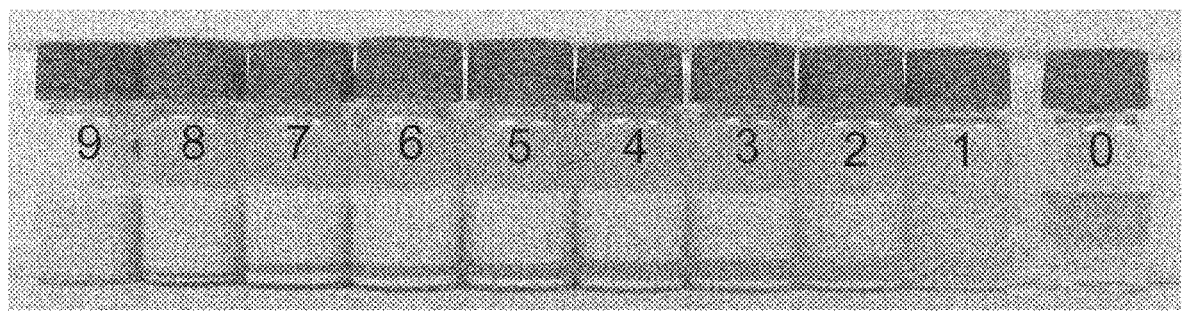
FIG. 1 shows the effect of a gradual, incremental weight increase of yeast concentration from 1, 2, 3, 4, 5, 6, 7, 8 and 9 on producing a 50 wt % oil+49-41 wt % water emulsion. Sample 0 represents 50 wt % water+50 wt % oil without added cells.

With reference to FIG. 1, the effect of gradual weight increments in yeast concentration (wt %) from 1, 2, 3, 4, 5, 6, 7, 8 and 9 on, producing 50 wt % oil+49-41 wt % water emulsion, are shown. Sample 0 is 50 wt % water+50 wt % oil without any added cells. By adding 1 wt % yeast to 49 wt % water+50 wt % oil (vial 1), the bulk oil phase is dispersed into droplets. Vial 2 shows an emulsion made with 2 wt % yeast+48 wt % water+50 wt % oil. Vial 3 shows an emulsion made with 3 wt % yeast+47 wt % water+50 wt % oil. Vial 4 shows an emulsion made with 4 wt % yeast+46 wt % water+50 wt % oil. Vial 5 shows an emulsion made with 5 wt % yeast+45 wt % water+50 wt % oil. Vial 6 shows an emulsion made with 6 wt % yeast+44 wt % water+50 wt % oil. Vial 7 shows an emulsion made with 7 wt % yeast+43 wt % water+50 wt % oil. Vial 8 shows an emulsion made with 8 wt % yeast+42 wt % water+50 wt % oil. Vial 9 shows an emulsion made with 9 wt % yeast+41 wt % water+50 wt % oil. By increasing the yeast concentration to 9 wt %, the oil phase (droplets) is uniformly distributed and not phase-separated. Samples were prepared with a vortex mixer.

Figure 2:
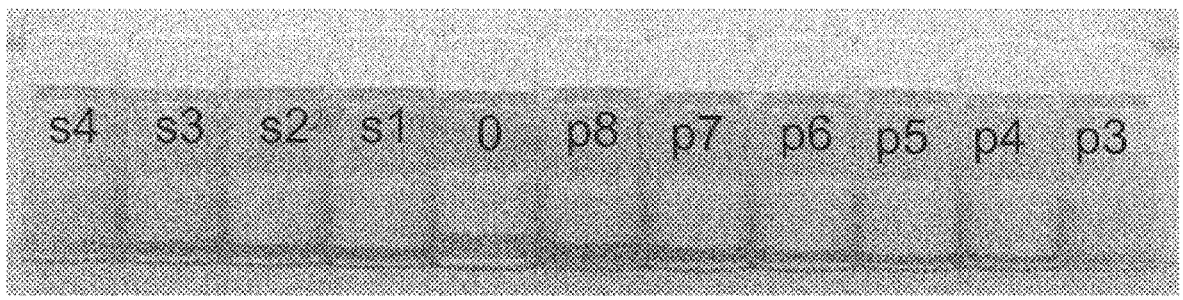
FIG. 2 shows the effect of a gradual, incremental increase of pH from 3 to 4, 5, 6, 7 and 8 as well as the effect of a gradual increase in salt concentration (i.e., 1, 2, 3 and 4 wt %) on the capability of 3 wt % yeast to produce a 50 wt % oil+47 wt % water emulsion.

With reference to FIG. 2, the effect of gradual increments in pH from 3 (p3) to pH 4 (p4), pH 5 (p5), pH 6 (p6), pH 7 (p7), and pH 8 (p8) as well as the effect of a gradual increase in salt concentration, e.g., 1 wt % (s1), 2 wt % (s2), 3 wt % (s3) and 4 wt % (s4) on the capability of 3 wt % yeast to produce a 50 wt % oil+47 wt % water emulsion are shown. By adding electrolyte (salts), the capability of yeast cells to form an oil-in-water emulsion is increased. As shown, sample 0 is 47 wt % water+50 wt % oil containing 3 wt % yeast without any electrolyte (salt). By adding 1 wt % salt (NaCl) (e.g., 46 wt % water+50 wt % oil vial s1), the capacity of yeast to form an emulsion increases, though there were no significant changes on emulsion formation in the system by adding 2 wt % salt, vial s2 (45 wt % water+50 wt % oil), 3 wt % salt, vial s3 (44 wt % water+50 wt % oil) or 4 wt % salt, vial s4 (43 wt % water+50 wt % oil). Likewise, by using a buffer solution, due to the effect of electrolytes, the capability of yeast to form an emulsion increases, and by moving the pH from 8 (p8) to pH 7 (p7), pH 6 (p6), pH 5 (p5), pH 4 (p4), and pH 3 (p3), the capacity of yeast to form 50 wt % water+47 wt % oil increases with the oil phase occupying a greater proportion of the emulsion volume. Samples were prepared with a vortex mixer.

Figure 3:
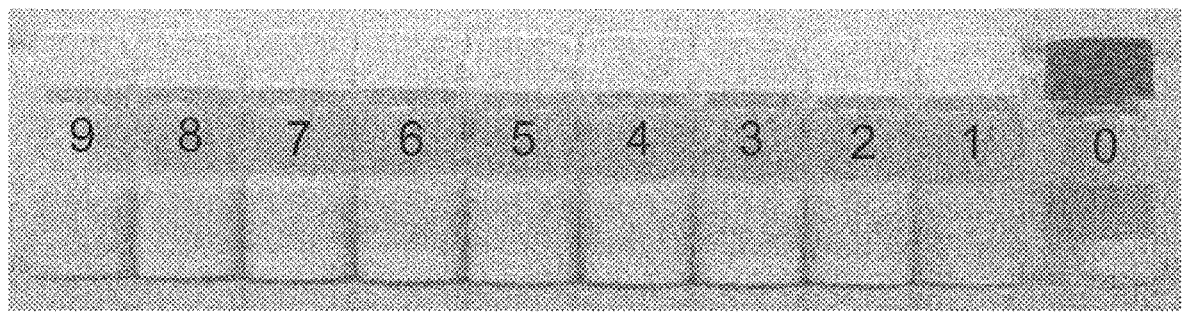
FIG. 3 shows the effect of a gradual, incremental weight increase of *Streptococcus thermophilus* concentration from 1, 2, 3, 4, 5, 6, 7, 8 and 9 on producing 50 wt % oil+49-41 wt % water emulsion. Sample 0 represents 50 wt % water+50 wt % oil without added cells.

With reference to FIG. 3, the effect of gradual increments in *Streptococcus thermophilus* concentration (wt %) from 1 2, 3, 4, 5, 6, 7, 8 and 9 on producing 50 wt % oil+49-41 wt % water emulsions are shown. Sample 0 is 50 wt % water+50 wt % oil without any added cells. By adding 1 wt % *Streptococcus thermophilus* to 49 wt % water+50 wt % oil (vial 1), the bulk oil phase is dispersed into droplets. Vial 2 shows an emulsion made with 2 wt % *Streptococcus thermophilus*+48 wt % water+50 wt % oil. Vial 3 shows an emulsion made with 3 wt % *Streptococcus thermophilus*+47 wt % water+50 wt % oil. Vial 4 shows an emulsion made with 4 wt % *Streptococcus thermophilus*+46 wt % water+50 wt % oil. Vial 5 shows an emulsion made with 5 wt % *Streptococcus thermophilus*+45 wt % water+50 wt % oil. Vial 6 shows an emulsion made with 6 wt % *Streptococcus thermophilus*+44 wt % water+50 wt % oil. Vial 7 shows an emulsion made with 7 wt % *Streptococcus thermophilus*+43 wt % water+50 wt % oil. Vial 8 shows an emulsion made with 8 wt % *Streptococcus thermophilus*+42 wt % water+50 wt % oil. Vial 9 shows an emulsion made with 9 wt % *Streptococcus thermophilus*+41 wt % water+50 wt % oil. By increasing the *Streptococcus thermophilus* concentration to 9 wt %, the oil phase occupies a greater proportion of the emulsion volume. Samples were prepared with a vortex mixer.

Figure 4:
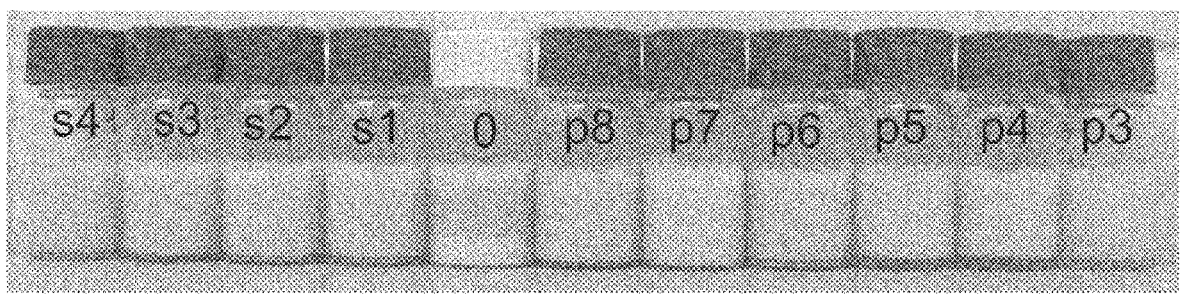
FIG. 4 shows the effect of a gradual, incremental increase of pH from 3, 4, 5, 6, 7 and 8 as well as the effect of a gradual increase in salt concentration (i.e., 1, 2, 3 and 4 wt %) on the capability of 3 wt % *Streptococcus thermophilus* to produce 50 wt % oil+47 wt % water emulsion.

With reference to FIG. 4, the effect of a gradual, incremental increase in pH from 3 (p3) to pH 4 (p4), pH 5 (p5), pH 6 (p6), pH 7 (p7) and pH 8 (p8) as well as the effect of a gradual increase in salt concentration from 1 wt % (s1) to 2 wt % (s2), 3 wt % (s3), and 4 wt % (s4) on the capability of 3 wt % *Streptococcus thermophilus* to produce 50 wt % oil+47 wt % water emulsion is shown. By adding electrolyte (salts), the capability of *Streptococcus thermophilus* cells to form an oil-in-water emulsion increases. As is shown, sample 0 is a 47 wt % water+50 wt % oil mixture containing 3 wt % *Streptococcus thermophilus* without any electrolyte (salt). By adding 1 wt % salt (NaCl) (e.g., 46 wt % water+50 wt % oil, vial s1), the capacity of *Streptococcus thermophilus* to form an emulsion increases, though there were no significant changes on the formation of the emulsion in the system by adding 2 wt % salt, vial s2 (45 wt % water+50 wt % oil), 3 wt % salt, vial s3 (44 wt % water+50 wt % oil), or 4 wt % salt, vial s4 (43 wt % water+50 wt % oil). Likewise, by using a buffer solution, due to the presence of the electrolyte, the capability of *Streptococcus thermophilus* to form an emulsion is increased in comparison to a sample without electrolyte (vial 0). However, by decreasing the pH from 8 (p8) to pH 7 (p7), pH 6 (p6), pH 5 (p5), pH 4 (p4), and pH 3 (p3), the capacity of *Streptococcus thermophilus* to form 50 wt % water+47 wt % oil slightly decreases, with the emulsion phase occupying a smaller proportion of the emulsion volume. Samples were prepared with a vortex mixer.

Figure 5:
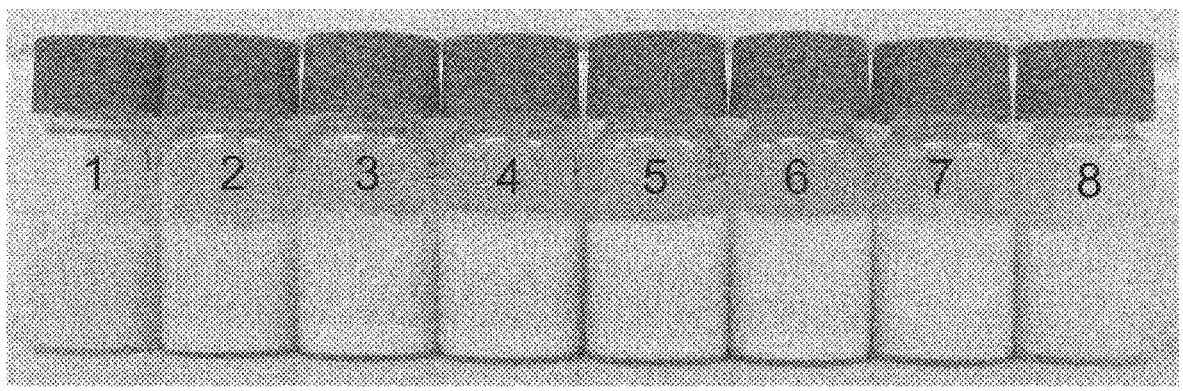
FIG. 5 shows the effect of a gradual, incremental weight increase of *Lactobacillus acidophilus* concentrations from 1 to 2, 3, 4, 5, 6, 7 and 8 on, producing a 50 wt % oil+49-42 wt % water emulsion.

With reference to FIG. 5, the effect of an incremental weight increase in *Lactobacillus acidophilus* concentration (wt %) from 1 to 2, 3, 4, 5, 6, 7 and 8 on, producing 50 wt % oil+49-42 wt % water emulsion is shown. Sample 0 is 50 wt % water+50 wt % oil without any added cells. By adding 1 wt % *Lactobacillus acidophilus* to 49 wt % water+50 wt % oil (vial 1), the bulk oil phase is dispersed into droplets. Vial 2 shows an emulsion made with 2 wt % *Lactobacillus acidophilus*+48 wt % water+50 wt % oil. Vial 3 shows an emulsion made with 3 wt % *Lactobacillus acidophilus*+47 wt % water+50 wt % oil. Vial 4 shows an emulsion made with 4 wt % *Lactobacillus acidophilus*+46 wt % water+50 wt % oil. Vial 5 shows an emulsion made with 5 wt % *Lactobacillus acidophilus*+45 wt % water+50 wt % oil. Vial 6 shows an emulsion made with 6 wt % *Lactobacillus acidophilus*+44 wt % water+50 wt % oil. Vial 7 shows an emulsion made with 7 wt % *Lactobacillus acidophilus*+43 wt % water+50 wt % oil. Vial 8 shows an emulsion made with 8 wt % *Lactobacillus acidophilus*+42 wt % water+50 wt % oil. By increasing the *Lactobacillus acidophilus* concentration to 8 wt %, the oil phase occupies a greater proportion of the emulsion volume. Samples were prepared with a vortex mixer.

Figure 6:
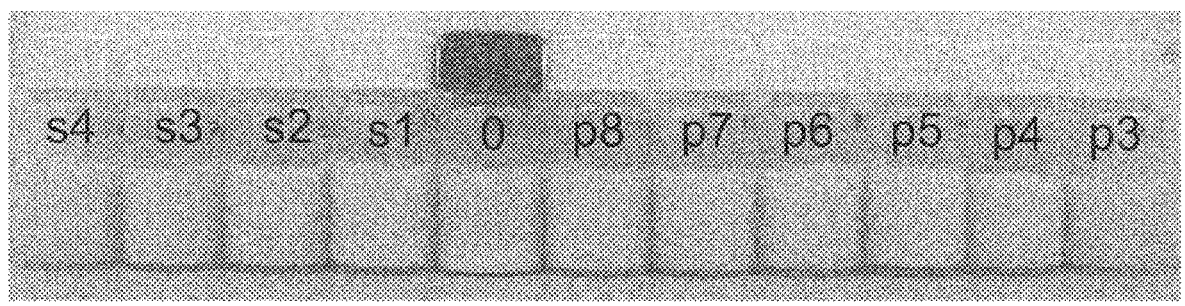
FIG. 6 shows the effect of a gradual, incremental increase of pH from 3 to 4, 5, 6, 7 and 8 as well as the effect of a gradual increase in salt concentration (i.e. 1, 2, 3 and 4 wt %) on the capability of 3 wt % *Lactobacillus acidophilus* to produce a 50 wt % oil+50 wt % water emulsion.

FIG. 6 shows the effect of an incremental increase in pH from 3 (p3) to pH 4 (p4), pH 5 (p5), pH 6 (p6), pH 7 (p7) and pH 8 (p8) as well as the effect of a gradual increase in salt concentration, e.g., 1 wt % (s1), 2 wt % (s2), 3 wt % (s3) and 4 wt % (s4), on the capability of 3 wt % *Lactobacillus acidophilus* to produce 50 wt % oil+47 wt % water emulsion. By adding electrolyte (salts), the capability of *Lactobacillus acidophilus* cells to form an oil-in-water emulsion increases. As is shown, sample 0 is 47 wt % water+50 wt % oil containing 3 wt % *Lactobacillus acidophilus* without any electrolyte (salt). By adding 1 wt % salt (NaCl) (e.g., 46 wt % water+50 wt % oil vial s1), the capacity of *Lactobacillus acidophilus* to form an emulsion increases. However, there were no significant changes in emulsion formation by adding 2 wt % salt, vial s2 (45 wt % water+50 wt % oil), 3 wt % salt, vial s3 (44 wt % water+50 wt % oil), or 4 wt % salt, vial s4 (43 wt % water+50 wt % oil). Likewise, by using a buffer solution, due to the effect of electrolytes, the capability of *Lactobacillus acidophilus* to form an emulsion increases as compared to the sample without electrolyte (vial 0). However, by decreasing the pH from 8 (p8) to pH 7 (p7), pH 6 (p6), pH 5 (p5), pH 4 (p4) and pH 3 (p3), the capacity of *Lactobacillus acidophilus* to form 50 wt % water+47 wt % oil slightly decreases, the oil phase occupies a smaller proportion of the emulsion volume. Samples were prepared with a vortex mixer.

Figure 7:
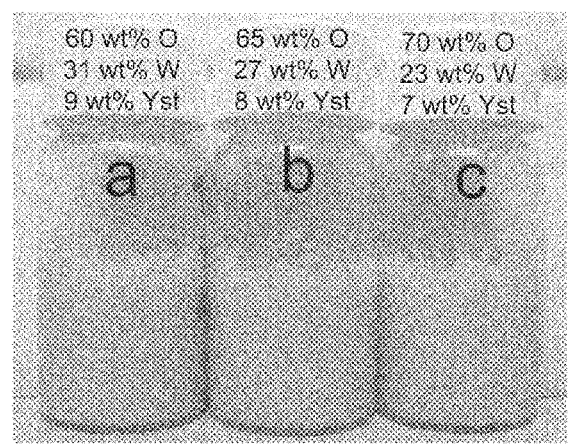
FIG. 7 shows three oil-in-water emulsions of different compositions: (a) an emulsion made 60 wt % oil+31 wt % water+9 wt % yeast, (b) an emulsion made with 65 wt % oil+27 wt % water+8 wt % yeast, and (c) an emulsion made with 70 wt % oil+23 wt % water+7 wt % yeast.

FIG. 7 presents three yeast-containing oil-in-water emulsions with different compositions. Sample (a) shows an emulsion made with 9 wt % yeast+60 wt % oil+31 wt % water. Sample (b) shows an emulsion made with 8 wt % yeast+65 wt % oil+27 wt % water. Sample (c) shows an emulsion made with 7 wt % yeast+70 wt % oil+23 wt % water. In this instance, to generate the emulsions, the oil phase was dispersed as oil droplets throughout the whole volume of the system. Therefore, in the emulsions with a lower oil content, a higher particle (cell) concentration was required to produce a higher number of oil droplets in order to increase the phase volume of the oil phase (e.g., with 60 wt % oil to produce a one-phase emulsion, 9 wt % yeast is required, but with a higher oil content, such as 65 wt % and 70 wt % oil, it is possible to use a lower yeast concentration, such as 8 wt % and 7 wt % to produce a single phase emulsion). Samples were prepared with a magnetic stirrer and a magnetic stir bar.

With reference to FIG. 8 (*a, b, c*), confocal laser scanning microscopy (CLSM) images show oil-in-water emulsions stabilized with yeast cells. The microstructure of the emulsions resembles that of typical oil-in-water emulsions, where the aqueous phase (water) forms a continuous phase containing the oil droplets. FIG. 8(*a*) shows an emulsion consisting of 7 wt % yeast+70 wt % oil+23 wt % water. FIG. 8(*b*) shows an emulsion made of 8 wt % yeast+65 wt % oil+27 wt % water. FIG. 8(*c*) shows an emulsion consisting of 9 wt % yeast+60 wt % oil+31 wt % water. The microstructure clearly indicates that by increasing the yeast cell concentration, the size of oil droplets is reduced.

Figure 9:
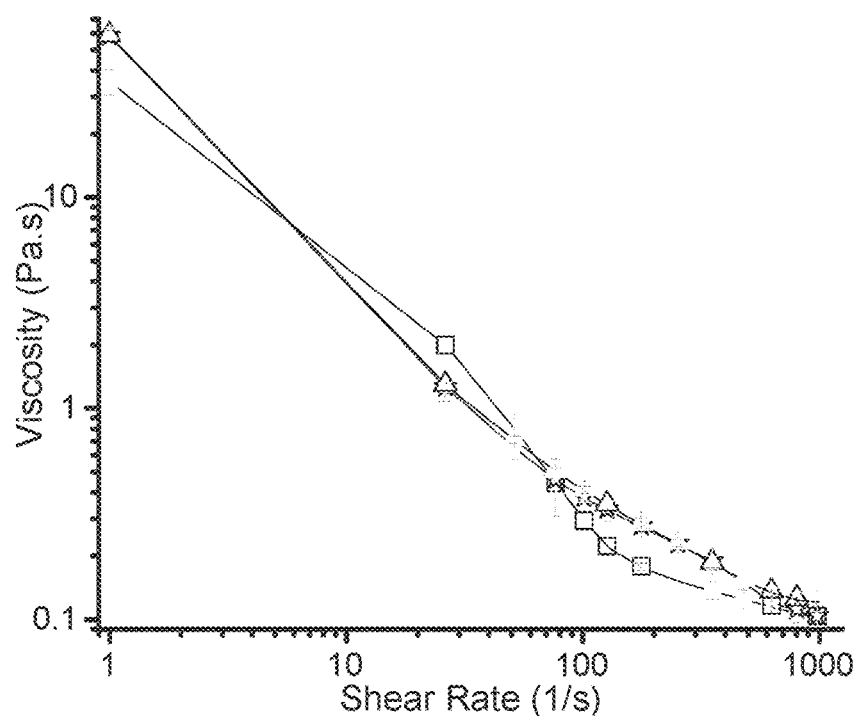
FIG. 9 depicts the shear viscosity versus the shear rate profile of emulsion samples of varying composition containing yeast (□: 7 wt % yeast+70 wt % oil+23 wt % water; ☆: 8 wt % yeast+65 wt % oil+27 wt % water; ∆: 9 wt % yeast+60 wt % oil+31 wt % water).

With reference to FIG. 9, the shear viscosity versus shear rate of the emulsions of (7 wt % yeast+70 wt % oil+23 wt % water), (8 wt % yeast+65 wt % oil+27 wt % water), and (9 wt % yeast+60 wt % oil+31 wt % water), illustrates the viscosity of samples with different compositions. In these tests, the apparent viscosity for all samples was measured at 25° C. at a shear rate in the range of 1 to 1000 $s^{-1}$. Each sample was first pre-sheared at a constant shear rate of 1 $s^{-1}$ for 60 seconds. Then, the sample was allowed to rest for 2 minutes on the testing tool before data was collected. The sample containing 7 wt % yeast showed a lower viscosity at a low shear rate as compared to that of samples containing 8 wt % and 9 wt % yeast. These samples containing 8 wt % and 9 wt % yeast showed similar viscosities.

Figure 10:
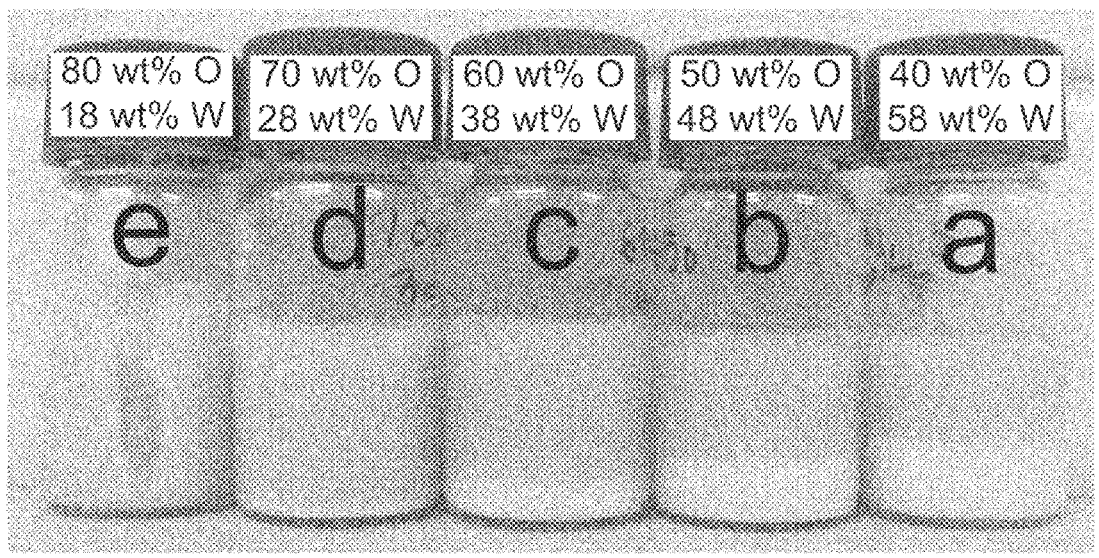
FIG. 10 shows the effect of an incremental increase of oil content (wt %) and corresponding decrease of water content (wt %) in emulsions containing 2 wt % *Streptococcus thermophilus*: (a) 40 wt % oil+58 wt % water, (b) 50 wt % oil+48 wt % water, (c) 60 wt % oil+38 wt % water, (d) 70 wt % oil+28 wt % water, (e) 80 wt % oil+18 wt % water.

With reference to FIG. 10, the effect of increasing oil content from 40 wt % to 80 wt % on the formation of one-phase emulsions containing 2 wt % *Streptococcus thermophilus* is illustrated. As the oil content increases and the water content decreases, the two-phase systems transform into a one-phase arrangement. As is shown, the emulsion volume increases with a gradual increase in oil content. Vial (a) contains 40 wt % oil+58 wt % water+2 wt % *Streptococcus thermophilus*. Vial (b) contains 50 wt % oil+48 wt % water+2 wt % *Streptococcus thermophilus*. Vial (c) contains 60 wt % oil+38 wt % water+2 wt % *Streptococcus thermophilus*. Vial (d) contains 70 wt % oil+28 wt % water+2 wt % *Streptococcus thermophilus*. Vial (e) contains 80 wt % oil+18 wt % water+2 wt % *Streptococcus thermophilus*. The sample in vial (e) transformed into a gel-like emulsion. Samples were prepared with a magnetic stirrer and a magnetic stir bar.

Figure 11:
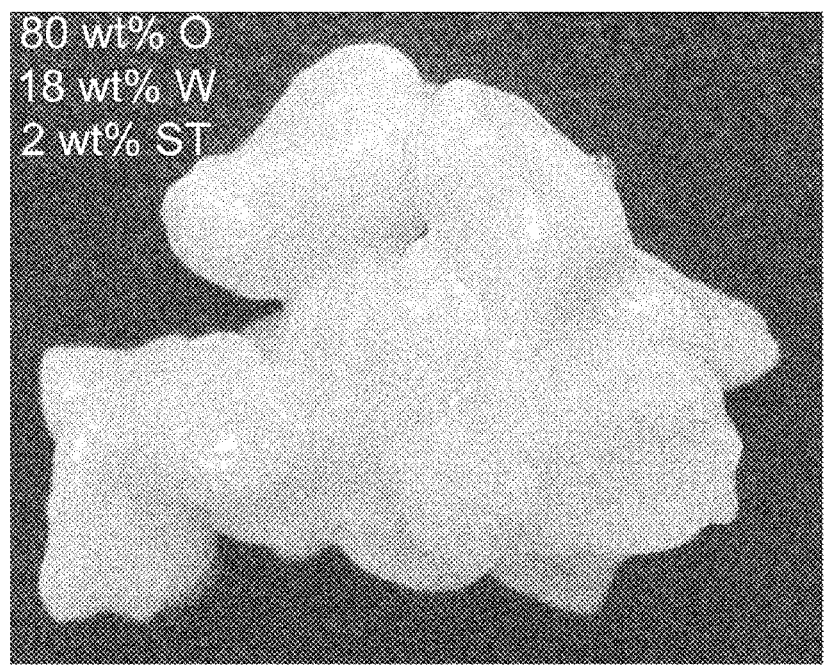
FIG. 11 shows an emulsion made with 80 wt % oil+18 wt % water+2 wt % *Streptococcus thermophilus*.

With reference to FIG. 11, the physical appearance of the emulsion made with 80 wt % oil+18 wt % water+2 wt % *Streptococcus thermophilus* (vial e, FIG. 10) is illustrated. The emulsion formed a gel which can support its own weight.

Figure 12:
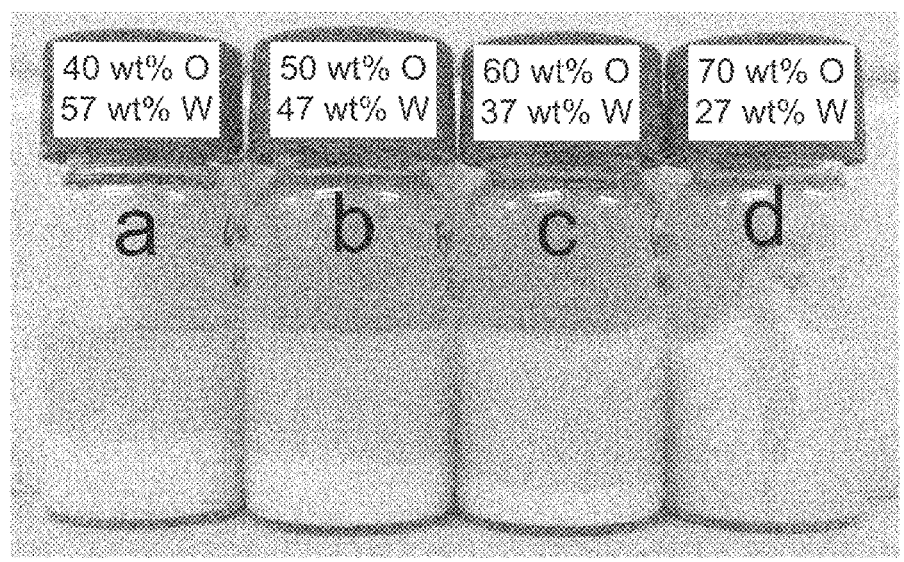
FIG. 12 shows the effect of an incremental increase of oil content (wt %) and corresponding decrease of water content (wt %) in emulsions containing 3 wt % *Streptococcus thermophilus*: (a) 40 wt % oil+57 wt % water, (b) 50 wt % oil+47 wt % water, (c) 60 wt % oil+37 wt % water, and (d) 70 wt % oil+27 wt % water.

With reference to FIG. 12, the effect of increasing oil content from 40 wt % to 70 wt % on the formation of one-phase emulsion containing 3 wt % *Streptococcus thermophilus* is illustrated. As the oil content increases and water content decreases, the two-phase systems transform into a one-phase arrangement. As is shown, the emulsion volume increases with a gradual increase in oil content. Vial (a) contains 40 wt % oil+57 wt % water+3 wt % *Streptococcus thermophilus*. Vial (b) contains 50 wt % oil+47 wt % water+3 wt % *Streptococcus thermophilus*. Vial (c) contains 60 wt % oil+37 wt % water+3 wt % *Streptococcus thermophilus*. Vial (d) contains 70 wt % oil+27 wt % water+3 wt % *Streptococcus thermophilus*. The sample in vial (d) transformed into a gel-like emulsion. Samples were prepared with a magnetic stirrer and a magnetic stir bar.

Figure 13:
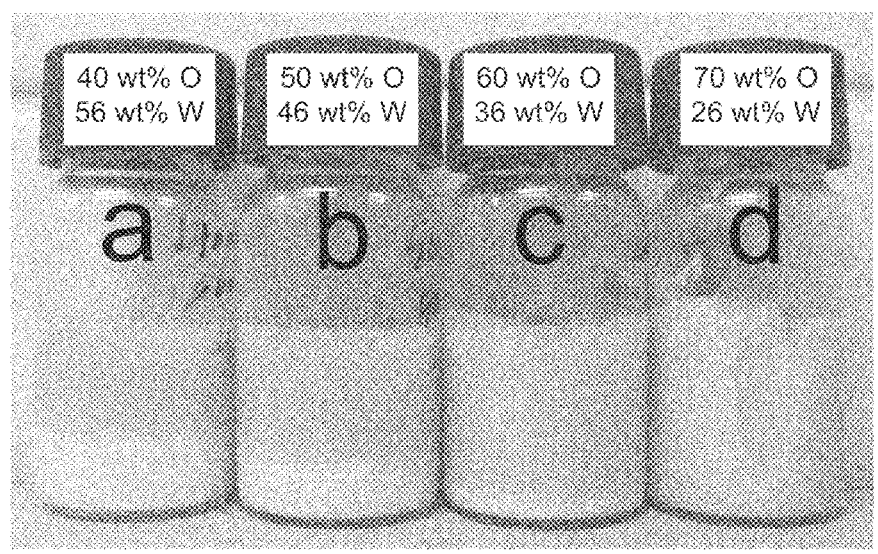
FIG. 13 shows the effect of an incremental increase of oil content (wt %) and corresponding decrease of water content (wt %) in emulsions containing 4 wt % *Streptococcus thermophilus*: (a) 40 wt % oil+56 wt % water, (b) 50 wt % oil+46 wt % water, (c) 60 wt % oil+36 wt % water, and (d) 70 wt % oil+26 wt % water.

With reference to FIG. 13, the effect of increasing oil content from 40 wt % to 70 wt % on the formation of one-phase emulsion containing 4 wt % *Streptococcus thermophilus* is illustrated. As the oil content increases and the corresponding water content decreases, the two-phase systems transform into a one-phase arrangement. As is shown, the emulsion volume increases with a gradual increase in oil content. Vial (a) contains 40 wt % oil+56 wt % water+4 wt % *Streptococcus thermophilus*. Vial (b) contains 50 wt % oil+46 wt % water+4 wt % *Streptococcus thermophilus*. Vial (c) contains 60 wt % oil+36 wt % water+4 wt % *Streptococcus thermophilus*. Vial (d) contains 70 wt % oil+26 wt % water+4 wt % *Streptococcus thermophilus*. The sample in vial (d) transformed into a gel-like emulsion. Samples were prepared with a magnetic stirrer and a magnetic stir bar.

Figure 14:
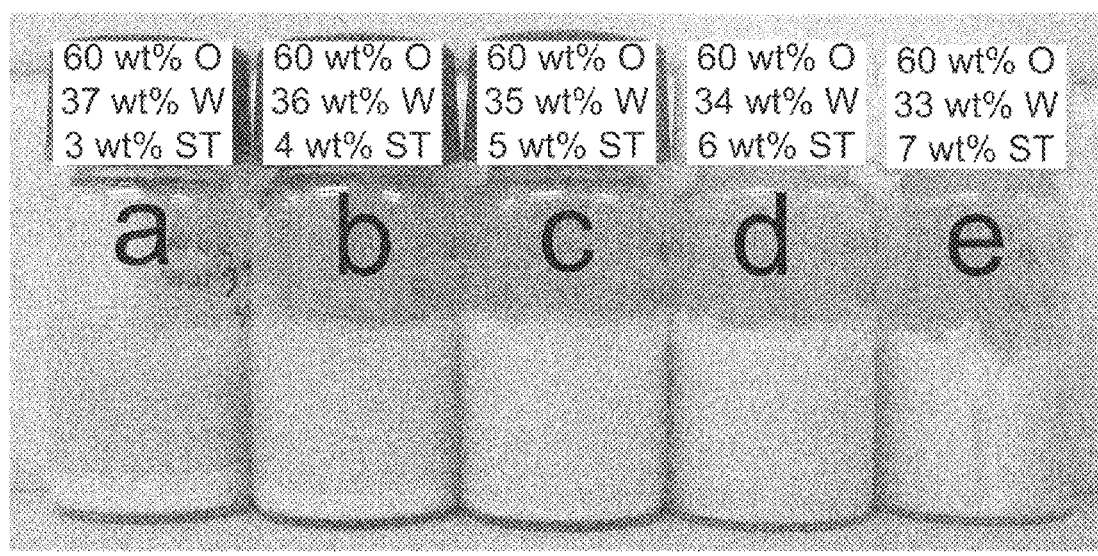
FIG. 14 shows the effect of an incremental increase of cell content (wt %) and corresponding decrease of water content (wt %) on emulsions made with 60 wt % oil: (a) 3 wt % *Streptococcus thermophilus*+37 wt % water+60 wt % oil, (b) 4 wt % *Streptococcus thermophilus*+36 wt % water+60 wt % oil, (c) 5 wt % *Streptococcus thermophilus*+35 wt % water+60 wt % oil, (d) 6 wt % *Streptococcus thermophilus*+34 wt % water+60 wt % oil, and (e) 7 wt % *Streptococcus thermophilus*+33 wt % water+60 wt % oil.

With reference to FIG. 14, the effect of increasing cell content (*Streptococcus thermophilus*) from 3 wt % to 7 wt % on the formation of one-phase emulsions containing 60 wt % oil is illustrated. As the cell content increases and the corresponding water content decreases, the two-phase system transform into a one-phase arrangement. As is shown, the emulsion phase volume increases with a gradual increase in *Streptococcus thermophilus* content. Vial (a) contains 3 wt % *Streptococcus thermophilus*+37 wt % water+60 wt % oil. Vial (b) contains 4 wt % *Streptococcus thermophilus*+36 wt % water+60 wt % oil. Vial (c) contains 5 wt % *Streptococcus thermophilus*+35 wt % water+60 wt % oil. Vial (d) contains 6 wt % *Streptococcus thermophilus*+34 wt % water+60 wt % oil. Vial (e) contains 7 wt % *Streptococcus thermophilus*+33 wt % water+60 wt % oil. The sample in vial (e) transformed into a gel-like emulsion. Samples were prepared with a magnetic stirrer and a magnetic stir bar.

Figure 15:
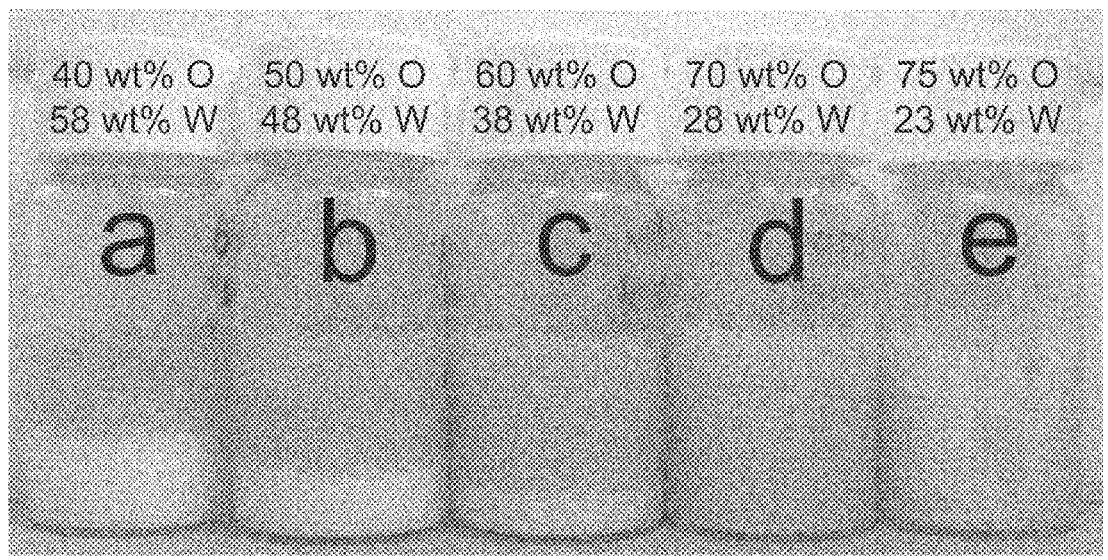
FIG. 15 shows the effect of an incremental increase of the oil content (wt %) and corresponding decrease of the water content (wt %) in emulsions containing 2 wt % *Lactobacillus acidophilus*: (a) 40 wt % oil+58 wt % water, (b) 50 wt % oil+48 wt % water, (c) 60 wt % oil+38 wt % water, (d) 70 wt % oil+28 wt % water, and (e) 75 wt % oil+23 wt % water.

With reference to FIG. 15, the effect of increasing oil content from 40 wt % to 75 wt % on the formation of one-phase emulsions containing 2 wt % *Lactobacillus acidophilus* is illustrated. As the oil wt % content increases and the corresponding water wt % content decreases, the two-phase system transforms into a one-phase arrangement. As is shown, the emulsion volume increases with a gradual increase in oil content. Vial (a) contains 40 wt % oil+58 wt % water+2 wt % *Lactobacillus acidophilus*. Vial (b) contains 50 wt % oil+48 wt % water+2 wt % *Lactobacillus acidophilus*. Vial (c) contains 60 wt % oil+38 wt % water+2 wt % *Lactobacillus acidophilus*. Vial (d) contains 70 wt % oil+28 wt % water+2 wt % *Lactobacillus acidophilus*. Vial (e) contains 75 wt % oil+23 wt % water+2 wt % *Lactobacillus acidophilus*. The sample in vial (e) transformed into a gel-like emulsion. Samples were prepared with a magnetic stirrer and a magnetic stir bar.

Figure 16:
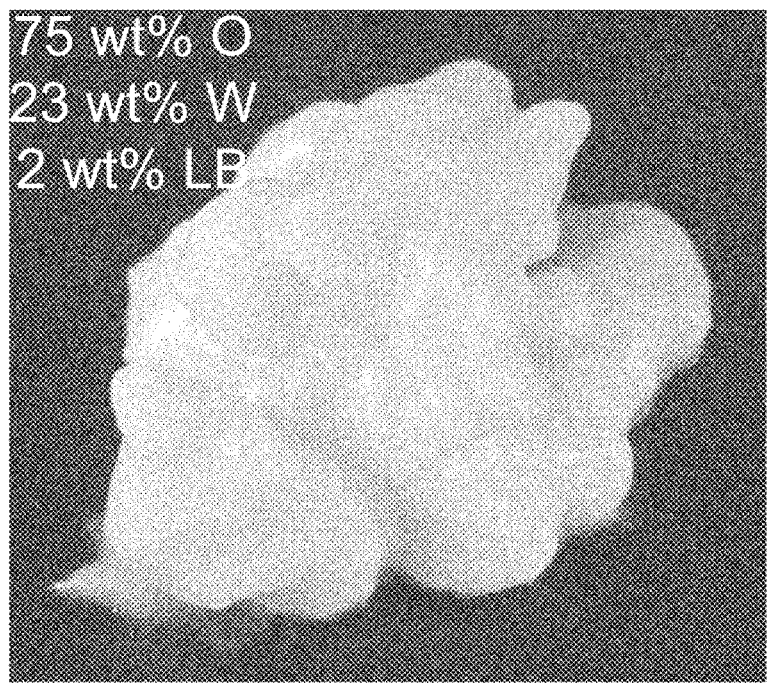
FIG. 16 shows an emulsion made with 75 wt % oil+23 wt % water+2 wt % *Lactobacillus acidophilus*.

With reference to FIG. 16, the physical appearance of an emulsion made with 75 wt % oil+23 wt % water+2 wt % *Lactobacillus acidophilus* (vial (e), FIG. 10) is illustrated. The emulsion formed a gel which can support its own weight.

Figure 17:
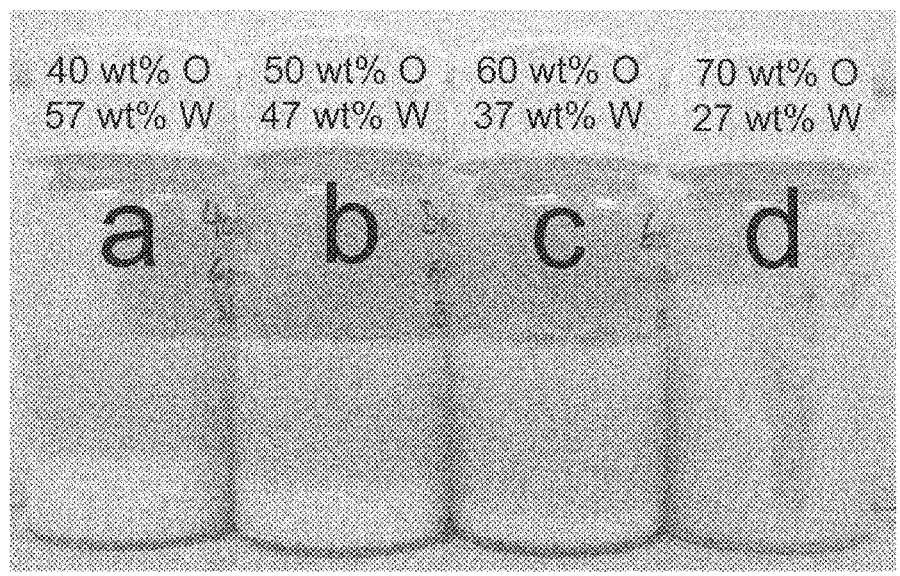
FIG. 17 shows the effect of an incremental increase of oil content (wt %) and the corresponding decrease of water content (wt %) in emulsions containing 3 wt % *Lactobacillus acidophilus*: (a) 40 wt % oil+57 wt % water, (b) 50 wt % oil+47 wt % water, (c) 60 wt % oil+37 wt % water, and (d) 70 wt % oil+27 wt % water.

With reference to FIG. 17, the effect of increasing oil content from 40 wt % to 70 wt % on the formation of one-phase emulsions containing 3 wt % *Lactobacillus acidophilus* is illustrated. As the oil wt % content increases and the corresponding water wt % content decreases, the two-phase system transforms into a one-phase arrangement. As is shown, the emulsion volume increases with a gradual increase in oil content. Vial (a) contains 40 wt % oil+57 wt % water+3 wt % *Lactobacillus acidophilus*. Vial (b) contains 50 wt % oil+47 wt % water+3 wt % *Lactobacillus acidophilus*. Vial (c) contains 60 wt % oil+37 wt % water+3 wt % *Lactobacillus acidophilus*. Vial (d) contains 70 wt % oil+27 wt % water+3 wt % *Lactobacillus acidophilus*. The sample in vial (d) transformed into a gel-like emulsion. Samples were prepared with a magnetic stirrer and a magnetic stir bar.

Figure 18:
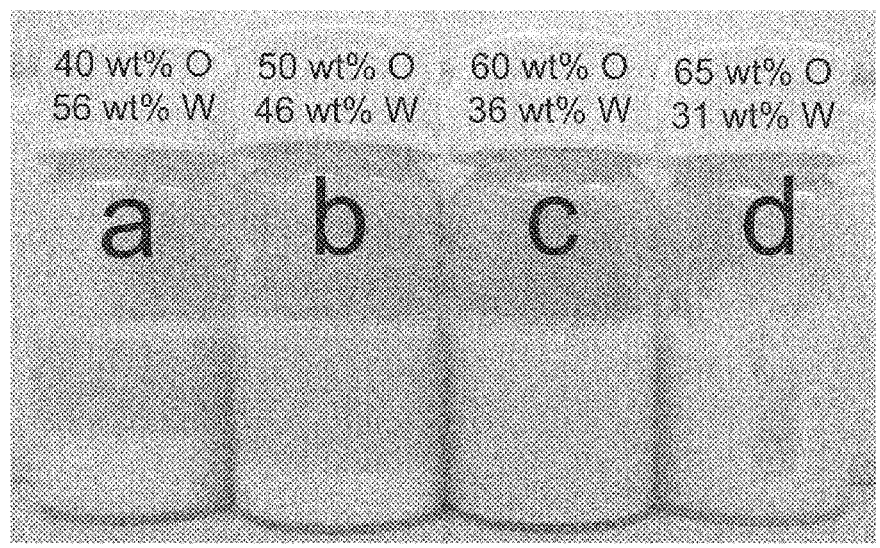
FIG. 18 shows the effect of an incremental increase of oil content (wt %) and a corresponding decrease of water content (wt %) in emulsions containing 4 wt % *Lactobacillus acidophilus*: (a) 40 wt % oil+56 wt % water, (b) 50 wt % oil+46 wt % water, (c) 60 wt % oil+36 wt % water, and (d) 65 wt % oil+31 wt % water.

With reference to FIG. 18, the effect of increasing oil content from 40 wt % to 65 wt % on formation of one-phase emulsions containing 4 wt % *Lactobacillus acidophilus* is illustrated. As the oil wt % content increases and the corresponding water wt % content decreases, the two-phase systems transform to a one-phase arrangement. As is shown, the emulsion volume increases with a gradual increase in oil content. Vial (a) contains 40 wt % oil+56 wt % water+4 wt % *Lactobacillus acidophilus*. Vial (b) contains 50 wt % oil+46 wt % water+4 wt % *Lactobacillus acidophilus*. Vial (c) contains 60 wt % oil+36 wt % water+4 wt % *Lactobacillus acidophilus*. Vial (d) contains 65 wt % oil+31 wt % water+4 wt % *Lactobacillus acidophilus*. The sample in vial (d) transformed into a gel-like emulsion. Samples were prepared with a magnetic stirrer and a magnetic stir bar.

Figure 19:
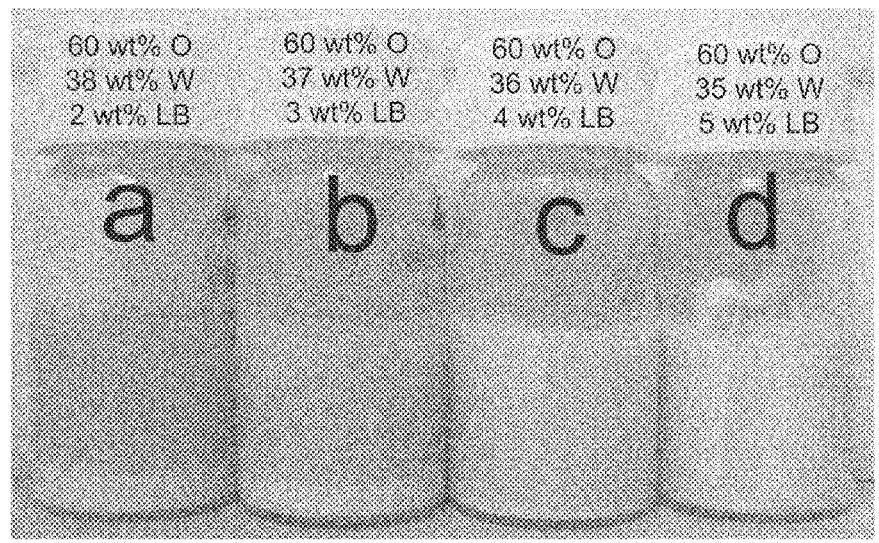
FIG. 19 shows the effect of an incremental increase of cell content (wt %) and the corresponding decrease of water content (wt %) on emulsions made with 60 wt % oil: (a) 2 wt % *Lactobacillus acidophilus*+38 wt % water+60 wt % oil, (b) 3 wt % *Lactobacillus acidophilus*+37 wt % water+60 wt % oil, (c) 4 wt % *Lactobacillus acidophilus*+36 wt % water+60 wt % oil, and (d) 5 wt % *Lactobacillus acidophilus*+35 wt % water+60 wt % oil.

With reference to FIG. 19, the effect of increasing cell content wt % (*Lactobacillus acidophilus*) from 2 wt % to 5 wt % on the formation of one-phase emulsions containing 60 wt % oil is illustrated. As the oil wt % content increases and the corresponding water wt % content decreases, the two-phase systems transform to a one-phase arrangement. As is shown, the oil phase volume increases by gradual increments with the *Lactobacillus acidophilus* content. Vial (a) contains 2 wt % *Lactobacillus acidophilus*+38 wt % water+60 wt % oil. Vial (b) contains 3 wt % *Lactobacillus acidophilus*+37 wt % water+60 wt % oil. Vial (c) contains 4 wt % *Lactobacillus acidophilus*+36 wt % water+60 wt % oil. Vial (d) contains 5 wt % *Streptococcus thermophilus*+35 wt % water+60 wt % oil. The sample in vial (d) transformed into a gel-like emulsion. Samples were prepared with a magnetic stirrer and a magnetic stir bar.

Figure 20:
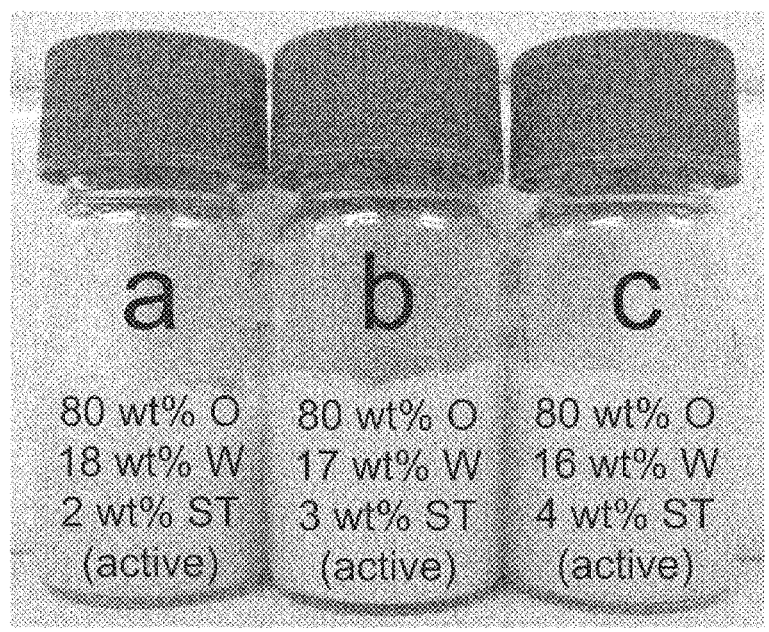
FIG. 20 shows oil-in-water emulsions made with active (live) *Streptococcus thermophilus*: vial (a) 80 wt % oil+18 wt % water+2 wt % active *Streptococcus thermophilus*, vial (b) 80 wt % oil+17 wt % water+3 wt % active *Streptococcus thermophilus*, and vial (c) 80 wt % oil+17 wt % water+3 wt % active *Streptococcus thermophilus*.

With reference to FIG. 20, it is shown that active (live) cells also are capable of forming one-phase oil-in-water emulsions. The emulsion in vial (a) is made of 80 wt % oil+18 wt % water+2 wt % active (live) *Streptococcus thermophilus*. The emulsion in vial (b) made is of 80 wt % oil+17 wt % water+3 wt % active (live) *Streptococcus thermophilus*. The emulsion in vial (c) is made of 80 wt % oil+16 wt % water+4 wt % active (live) *Streptococcus thermophilus*.

Figure 21:
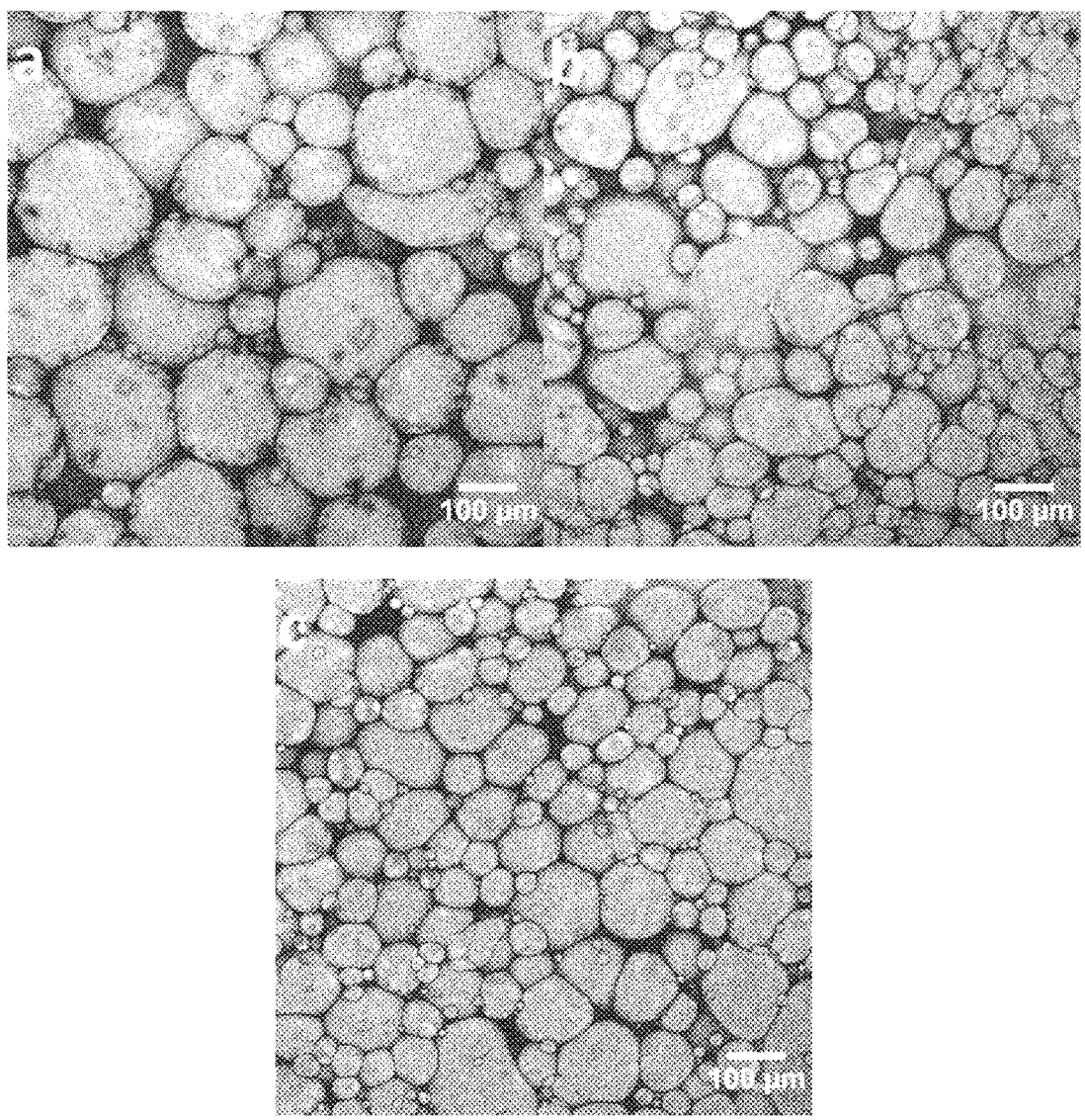
FIG. 21 (a, b, c) shows the confocal laser scanning microscopy (CLSM) images of oil-in-water emulsions stabilized with active *Streptococcus thermophilus* cells.

With reference to FIG. 21 (*a, b, c*), the CLSM images show oil-in-water emulsions made with active (live) *Streptococcus thermophilus* cells. The FIG. 21-*a* emulsion is made of 80 wt % oil+18 wt % water+2 wt % active *Streptococcus thermophilus*. The FIG. 21-*b* emulsion is made of 80 wt % oil+17 wt % water+3 wt % active *Streptococcus thermophilus*. The FIG. 21-*c* emulsion is made of 80 wt % oil+16 wt % water+4 wt % active *Streptococcus thermophilus*. Due to the high proportion of the oil (80 wt %) the oil droplets are in a close-packed arrangement, and as the *Streptococcus thermophilus* weight concentration increases, the number of oil droplets increase and the oil droplet size decreases.

With reference to FIG. 22, shear viscosity versus shear rate is shown for emulsions made of (2 wt % active *Streptococcus thermophilus*+80 wt % oil+18 wt % water), (3 wt % active *Streptococcus thermophilus*+80 wt % oil+17 wt % water) and (4 wt % active *Streptococcus thermophilus*+80 wt % oil+16 wt % water). In these tests, the apparent viscosity for all samples was measured at 25° C. at shear rates in the range of 1 to 1000 $s^{-1}$. Each sample was first pre-sheared at a constant shear rate of 1 $s^{-1}$ for 60 seconds. Then, each sample was allowed to rest for 2 minutes on the testing tool before data was collected. The sample containing 2 wt % *Streptococcus thermophilus* showed a lower viscosity at a low shear rate in comparison to samples containing 4 wt % and 3 wt % yeast. At higher shear rates, samples containing 2 wt % and 3 wt % *Streptococcus thermophilus* showed similar viscosities, lower than that of samples containing 4 wt % *Streptococcus thermophilus*.

With reference to FIG. 23, the CLSM image shows an oil-in-water emulsion of 80 wt % oil+18 wt % water+2 wt % *Streptococcus thermophilus*. Due to the high proportion of oil (80 wt %), the oil droplets are in a close-packed arrangement.

With reference to FIG. 24, the CLSM image shows an oil-in-water emulsion comprised of 70 wt % oil+27 wt % water+3 wt % *Streptococcus thermophilus*. Its microstructure resembles a typical oil-in-water emulsion, where the water forms a continuous phase containing the oil droplets.

With reference to FIG. 25, the CLSM image shows an oil-in-water emulsion comprised of 70 wt % oil+26 wt % water+4 wt % *Streptococcus thermophilus*. Its microstructure resembles a typical oil-in-water emulsion where the water forms a continuous phase containing the oil droplets. As the cell concentration increases to 4 wt % in this system, the oil droplets become more uniform in size.

With reference to FIG. 26, the CLSM image shows an oil-in-water emulsion comprised of 60 wt % oil+33 wt % water+7 wt % *Streptococcus thermophilus*. Its microstructure resembles a typical oil-in-water emulsion, where the water forms a continuous phase containing the oil droplets. As the cell concentration increases to 7 wt % in this system, the oil droplets become more uniform and fill the entire emulsion.

With reference to FIG. 27, shear viscosity versus shear rate is shown for emulsions made of (2 wt % *Streptococcus thermophilus*+80 wt % oil+18 wt % water), emulsions made of (3 wt % *Streptococcus thermophilus*+70 wt % oil+27 wt % water), emulsions made of (4 wt % *Streptococcus thermophilus*+70 wt % oil+26 wt % water) and emulsions made of (7 wt % *Streptococcus thermophilus*+60 wt % oil+33 wt % water). In these tests, the apparent viscosity for all samples was measured at 25° C. at shear rates within the range of 1 to 1000 $s^{-1}$. Each sample was first pre-sheared at a constant shear rate of 1 $s^{-1}$ for 60 seconds. Then, each sample was allowed to rest for 2 minutes on the testing tool before data was collected. The sample containing 4 wt % *Streptococcus thermophilus*+70 wt % oil+26 wt % water showed the highest viscosity overall in comparison with that of other samples. The sample containing 3 wt % *Streptococcus thermophilus*+70 wt % oil+27 wt % water showed the lowest viscosity. The samples containing 80 wt % oil and 60 wt % oil, despite their different oil contents, exhibit similar viscosity profiles at a low shear rate and show similar trends with regard to viscosity changes as a function an applied shear rate. However, at a high shear rate, the emulsion containing 60 wt % oil shows the highest viscosity and the sample containing 80 wt % oil shows the lowest viscosity.

With reference to FIG. 28, the CLSM image shows an oil-in-water emulsion containing 75 wt % oil+23 wt % water+2 wt % *Lactobacillus acidophilus*. Due to the high proportion of the oil (75 wt %), the oil droplets are in a close-packed arrangement.

With reference to FIG. 29, the CLSM image shows an oil-in-water emulsion containing 70 wt % oil+27 wt % water+3 wt % *Lactobacillus acidophilus*. Some of the oil droplets are in a close-packed arrangement.

With reference to FIG. 30, the CLSM image shows an oil-in-water emulsion containing 65 wt % oil+31 wt % water+4 wt % *Lactobacillus acidophilus*. Its microstructure resembles a typical oil-in-water emulsion, where the water forms a continuous phase containing the oil droplets.

With reference to FIG. 31, the CLSM image shows an oil-in-water emulsion containing 60 wt % oil+35 wt % water+5 wt % *Lactobacillus acidophilus*. Its microstructure resembles a typical oil-in-water emulsion, where the water forms a continuous phase containing the oil droplets.

With reference to FIG. 32, shear viscosity versus shear rate is shown for emulsions comprised of (2 wt % *Lactobacillus acidophilus*+75 wt % oil+23 wt % water), (3 wt % *Lactobacillus acidophilus*+70 wt % oil+27 wt % water), (4 wt % *Lactobacillus acidophilus*+65 wt % oil+31 wt % water) and (5 wt % *Lactobacillus acidophilus*+60 wt % oil+35 wt % water). Each sample was first pre-sheared at a constant shear rate of 1 $s^{-1}$ for 60 seconds. Then, each sample was allowed to rest for 2 minutes on the testing tool before data was collected. The sample containing 3 wt % *Lactobacillus acidophilus*+70 wt % oil+27 wt % water showed the highest viscosity at a low shear rate in comparison with other samples. The sample containing 5 wt % *Lactobacillus acidophilus*+60 wt % oil+35 wt % water showed the lowest viscosity. The samples containing 75 wt % oil and 65 wt % oil, despite their different oil contents, exhibited similar viscosities at a low shear rate up to around 9 $s^{-1}$. However, they showed a different trend with regard to changes in viscosity at a higher shear rate. The sample containing 65 wt % oil and 4 wt % *Lactobacillus acidophilus* showed a higher viscosity as compared to that of the sample containing 75 wt % oil with 2 wt % *Lactobacillus acidophilus*. The emulsion containing 60 wt % oil with 5 wt % *Lactobacillus acidophilus* showed the lowest viscosity at a low shear rate but the highest viscosity at a high shear rate. This difference in viscosity is related to the presence of different quantities of bacterial cells and the overall compositions of different emulsions.

With reference to FIG. 33 (a, b, c), each CLSM image shows an oil droplet in an oil-in-water emulsions stabilized with different cells adsorbed at oil-water interface. FIG. 33-a shows *Streptococcus thermophilus* cells, FIG. 33-b shows *Lactobacillus acidophilus* cells and FIG. 33-c shows yeast cells adsorbed at oil-water interface.

For the above examples, the following conditions were applied.

Material

Baker's yeast (*Sacchromyces cerevisiae*) was supplied by Lesaffre, (Red Star brand) (Milwaukee, Wis., USA). *Lactobacillus acidophilus* and *Streptococcus thermophilus* were purchased from Custom Probiotics (Glendale, Calif., USA). Salt (NaCl), citric acid and sodium phosphate dibasic ($Na_2HPO_4$) were supplied by Fisher Scientific (Ottawa, ON, Canada). Distilled water was used throughout. Olive oil was purchased from a local supermarket.

Buffer Solution

Buffer solutions with a pH range from 3 to 8 were obtained by combining appropriate volumes of 0.1M citric acid with 0.2M sodium phosphate dibasic solutions.

Cell Preparation

Although treatment of the cells is optional, it is possible to use live (active) cells for preparation of emulsions. However, in order to prevent the biological activity of the cells within the emulsion, the following protocol for cell preparation was used to inactivate the cells. The yeast cells, *Lactobacillus acidophilus*, or *Streptococcus thermophilus* were suspended in distilled water at a concentration of 10 wt % in a sealed screw cap glass bottle. The cell-containing bottles were placed in a waterbath at 95° C. for 10 min and shaken regularly every 5-6 min for 15-20 sec. Then, the glass bottle was removed from the waterbath and left at room temperature to cool in order for centrifugation. The supernatant was discarded and the sediment was transferred to a 50 ml centrifuge tube and washed 5-7 times with about 30 ml of distilled water by repeated re-suspension/centrifugation cycles 5 minutes for yeast and 30 minutes for *Lactobacillus acidophilus* and *Streptococcus thermophilus* at 3500 rpm. At the final stage of centrifugation, a clear transparent supernatant (water) and a homogeneous and uniform sediment containing cells were obtained. Any method known to a person of ordinary skill in the art for inactivating said cells may be used.

The majority of the examples were prepared with inactive cells, however when active cells were utilized in the examples, the use of active cells are clearly described.

Mixing Procedure

Two procedures were adopted for mixing; either mixing was performed with a vortex mixer (Fisher Scientific, cat No 02215570, Nepean, ON, Canada) or with a magnetic stirrer (IKA® C-MAG HS7) and a magnetic stir bar 25 mm in length and 9 mm in width. In both cases, the oil phase was mixed gradually with the entire aqueous phase consisting of water and cells. When a vortex mixer was employed, the addition of oil and mixing were performed in consecutive stages of oil addition (around 1 gram) followed by 20 seconds of mixing with the vortex mixer at 3000 rpm; this procedure was continued until all oil was added and mixed within the entire mixture. When a magnetic stirrer and a magnetic stir bar were used, the whole aqueous phase (water+cells) was placed in a vial and the oil phase was added drop-wise at a rate of 1 $cm^3$ per 90 to 100 seconds to the aqueous phase along with the magnetic stirrer mixing at a rate of 448 to 560 revolution per minute. Mixing was continued until the entire oil phase was incorporated into the mixture. Incomplete mixing fails to produce the emulsion. Also, if the aqueous phase changes from a continuous phase to a dispersed phase, the emulsion is not formed.

Any mixing procedure known to a person of ordinary skill in the art resulting in a stable emulsion as defined herein is applicable.

Small-Deformation Rheometry

A Physica MCR 301 rheometer (Anton Paar GmbH, Graz, Austria), equipped with a Peltier plate temperature control unit (P-PTD 200), was used to perform small-deformation oscillatory rheometery. All measurements were carried out with a cone and plate geometry (CP 25-1/TG) with a diameter of 25 mm, angle 1°, and an operation gap of 48 µm.

Confocal Laser Scanning Microscopy (CLSM)

Confocal laser scanning microscopy was performed using an upright Zeiss LSM 510 (Carl Zeiss, Toronto, ON, Canada). The CLSM was operated in fluorescent mode with an Ar laser source (488 nm). The emission spectra were collected with 1 channel set at 650 nm. No fluorescent labeling was used for cell-containing samples, since autofluorescence properties of the cells and olive oil were sufficient for CLSM observation. For characterization, 10×, 20× and 63× water emersion objective lenses were used. Images were recorded at 25° C. at a resolution of 1024×1024 pixels. Image optimization was performed using the LSM 510's built-in image analysis software. Images shown herein are representative of the microstructure seen for a given composition.

With the use of cells, it is possible to produce a stable oil-in-water emulsion with the internal-phase ratio more than 0.71. In one instance with *Streptococcus thermophilus*, the internal phase can reach ca. 0.80 (80 wt %+18 wt % water+2 wt % *Streptococcus thermophilus*) and with *Lactobacillus acidophilus*, the internal phase can reach ca. 0.75 (75 wt % oil+23 wt % water+2 wt % *Lactobacillus acidophilus*). This means that although the oil phase has a higher volume that that of the aqueous phase, the oil phase remains as a discontinuous or dispersed phase within the continuous aqueous phase and the emulsion remains stable.

Although the above examples are on a laboratory scale, a person of ordinary skill in the art reading the above examples will be able to carry out the present invention on an industrial scale.

As many changes can be made to the preferred embodiment of the invention without departing from the scope thereof; it is intended that all matter contained herein be considered illustrative of the invention and not in a limiting sense.

The invention claimed is:

1. A single-phase stable edible emulsion, consisting of oil, water and a stabilizer, said stabilizer being prepared by a process consisting of:
   i) suspending a biologically active (live) single-cell microorganism in distilled water resulting in a suspension,
   ii) heating said suspension to 95° C. for 10 minutes with shaking every 5-6 min for 15-20 sec resulting in a supernatant and sediment,
   iii) cooling and removing said supernatant, and
   iv) washing said cooled sediment followed by centrifugation and washing until a homogeneous and uniform sediment containing only non-lysed biologically inactive (dead) microorganism is obtained,
   wherein said stabilizer is deactivated into a biologically inactive (dead) single-cell microorganism, said stabilizer and said single-phase stable edible emulsion being free of any biologically active (live) single-cell microorganism, wherein said single-phase stable edible emulsion is prepared without added heat, said single-phase stable edible emulsion being food-grade.

2. The single-phase stable edible emulsion of claim 1, wherein said single-cell microorganism is selected from the group consisting of yeast, *Lactobacillus, Streptococcus*, and combinations thereof.

3. The single-phase stable edible emulsion of claim 2, wherein the yeast is Baker's yeast, the microorganism of the genus *Lactobacillus* is *Lactobacillus acidophilus*, and the microorganism of the genus *Streptococcus* is *Streptococcus thermophilus*.

4. The single-phase stable edible emulsion of claim 1, wherein said oil is from about 0.01 wt % to about 99 wt %, and said biologically inactive single-cell microorganism is from about 0.001 wt % to about 10 wt %.

5. A single-phase stable edible emulsion, consisting of oil, water and a stabilizer, and at least one of:
   a) a biopolymer, protein, polysaccharide or a combination thereof in an amount of from about 0.0001 wt % to about 10 wt %;
   b) at least one surfactant, surface active material or a combination thereof, in an amount of from about 0.0001 wt % to about 10 wt % of the emulsion; and
   c) at least one agent selected from the group consisting of a flavouring agent, colouring agent, an acidulant, a salt, an antioxidant, a preservative, a biopolymer, an emulsifier, a vitamin, a mineral, a fragrant agent, and combinations thereof; wherein
said stabilizer being prepared by a process consisting of:
i) suspending a biologically active (live) single-cell microorganism selected from the group consisting of Baker's yeast, *Lactobacillus acidophilus, Streptococcus thermophilus*, and combinations thereof, in distilled water resulting in a suspension,
ii) heating said suspension to 95° C. for 10 minutes with shaking every 5-6 min for 15-20 sec resulting in a supernatant and sediment,
iii) cooling and removing said supernatant, and
iv) washing said cooled sediment followed by centrifugation and washing until a homogeneous and uniform sediment containing only non-lysed biologically inactive (dead) microorganism is obtained,
wherein said stabilizer is deactivated into a biologically inactive (dead) single-cell microorganism, said stabilizer and said single-phase stable edible emulsion being free of any biologically active (live) single-cell microorganism,
wherein said single-phase stable edible emulsion is prepared without added heat, said single-phase stable edible emulsion being food-grade.

6. The single-phase stable edible emulsion of claim 5, wherein said acidulant is selected from the group consisting of ascorbic acid, benzoic acid, sorbic acid, acetic acid and combinations thereof in the acid or salt form.

7. The single-phase stable edible emulsion of claim 1, wherein said oil is present in an amount of:
   i) about 1 wt % to about 80 wt %;
   and said biologically inactive single cell microorganism is present in an amount of:
   i.) about 1 wt % to about 8 wt %.

8. The single-phase stable edible emulsion of claim 5, wherein said biopolymer, protein, polysaccharide or a combination thereof is present in an amount of from about 0.001 wt % to about 5 wt %.

9. The single-phase stable edible emulsion of claim 5, wherein said at least one surfactant, surface active material or a combination thereof is present in an amount of from about 0.001 wt % to about 5 wt %.

10. The single-phase stable edible emulsion of claim 5, wherein said biopolymer, protein, polysaccharide or a combination thereof is present in an amount of from about 0.01 wt % to about 4 wt %.

11. The single-phase stable edible emulsion of claim 5, wherein said at least one surfactant, surface active material or a combination thereof is present in an amount of from about 0.01 wt % to about 4 wt %.

12. The single-phase stable edible emulsion of claim 1, wherein said single-cell microorganism is selected from the group consisting of *Lactobacillus, Streptococcus*, and combinations thereof.

13. The single-phase stable edible emulsion of claim 12, wherein the microorganism of the genus *Lactobacillus* is *Lactobacillus acidophilus* and the microorganism of the genus *Streptococcus* is *Streptococcus thermophilus*.

14. A single-phase stable edible emulsion, consisting of oil, water and a stabilizer, wherein said stabilizer is a biologically inactive (dead) single-cell microorganism, said stabilizer prepared by a process consisting of suspending a biologically active (live) single-cell microorganism in distilled water, heating said suspension to 95° C. for 10 minutes with shaking every 5-6 minutes for 15-20 seconds resulting in a supernatant and sediment, cooling, removing said supernatant and washing said cooled sediment followed by centrifugation and washing until a homogeneous and uniform sediment containing only non-lysed inactive (dead) microorganism is obtained, said stabilizer being free of any biologically active (live) single-cell microorganism, wherein said emulsion is prepared without added heat, said emulsion being food-grade.

15. The single-phase stable edible emulsion of claim 1, wherein said emulsion is in a liquid state.

16. The single-phase stable edible emulsion of claim 14, wherein said emulsion is in a liquid state.

17. The single-phase stable edible emulsion of claim 1, wherein said oil is present in an amount of:
   i) about 50 wt % to about 80 wt %,
   and said biologically inactive single cell microorganism is present in an amount of:
   i) about 2 wt % to about 7 wt %.

* * * * *